US007776057B2

(12) United States Patent
Laufer et al.

(10) Patent No.: US 7,776,057 B2
(45) Date of Patent: *Aug. 17, 2010

(54) METHODS AND DEVICES FOR TISSUE RECONFIGURATION

(75) Inventors: Michael D. Laufer, Menlo Park, CA (US); Jeffrey C. Cerier, Franklin, MA (US); Amos Cruz, Franklin, MA (US); Jonathan O'Keefe, Scituate, MA (US); Richard Andrews, Lincoln, RI (US); Vincent A. Puicci, Jr., Spencer, MA (US); Michael Barenboym, Ashland, MA (US); Neal H. Marshall, Bolton, MA (US); Randal B. Chinnock, Sturbridge, MA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1288 days.

This patent is subject to a terminal disclaimer.

(21) Appl. No.: 10/992,228

(22) Filed: Nov. 19, 2004

(65) Prior Publication Data

US 2006/0025789 A1 Feb. 2, 2006

Related U.S. Application Data

(63) Continuation-in-part of application No. 09/859,579, filed on May 18, 2001, now Pat. No. 6,821,285, which is a continuation-in-part of application No. 09/574,424, filed on May 19, 2000, now Pat. No. 6,494,888, which is a continuation-in-part of application No. 09/520,273, filed on Mar. 7, 2000, now Pat. No. 6,663,639, and a continuation-in-part of application No. 09/519,945, filed on Mar. 7, 2000, now Pat. No. 6,506,196.

(60) Provisional application No. 60/306,652, filed on Jul. 18, 2001, provisional application No. 60/140,492, filed on Jun. 22, 1999.

(51) Int. Cl.
*A61B 17/04* (2006.01)
(52) U.S. Cl. ..................................................... 606/139
(58) Field of Classification Search ................. 606/139, 606/144, 148, 150, 153, 205–210, 219–221, 606/232
See application file for complete search history.

(56) References Cited

U.S. PATENT DOCUMENTS 1,343,289 A  6/1920  Suchy (Continued)

FOREIGN PATENT DOCUMENTS

EP   0 480 428   4/1992

(Continued)

OTHER PUBLICATIONS

Boerema, "Hiatus Hernia: Repair by right-sided, subhepatic, anterior gastropexy," *Surgery* (1969) 65:884-893.

(Continued)

*Primary Examiner*—Kevin T Truong

(57) ABSTRACT

A method includes advancing an apparatus having an elongated member transorally into the stomach. The apparatus includes a distal end effector having first and second members configured to engage tissue. The first and second members are movable relatively toward one another generally in a first plane. The method includes moving the distal end effector relative to the elongated member in the first plane such that the distal end effector is retroflexed out of alignment with the elongated member to position the first and second members for engagement with the tissue. At least one of the first and second members carries a fixation device for fixing engaged portions of tissue together.

20 Claims, 8 Drawing Sheets

U.S. PATENT DOCUMENTS

| | | |
|---|---|---|
| 1,548,250 A | 8/1925 | Bobner |
| 2,104,885 A | 1/1938 | robbins |
| 2,199,025 A | 4/1940 | Conn |
| 3,216,424 A | 11/1965 | William |
| 3,399,432 A | 9/1968 | Merser |
| 3,470,875 A | 10/1969 | Johnson |
| 3,551,987 A | 1/1971 | Wilkinson |
| 3,636,594 A | 1/1972 | Faivre et al. |
| 3,638,653 A | 2/1972 | Berry |
| 3,734,375 A | 5/1973 | Bone et al. |
| 3,749,085 A | 7/1973 | Wilson et al. |
| 3,842,840 A | 10/1974 | Schweizer |
| 3,875,648 A | 4/1975 | Bone |
| 3,900,925 A | 8/1975 | La Torraca |
| 3,901,244 A | 8/1975 | Schweizer |
| 3,933,291 A | 1/1976 | Stephenson |
| 3,946,740 A | 3/1976 | Bassett |
| 4,006,747 A | 2/1977 | Kronenthal et al. |
| 4,014,492 A | 3/1977 | Rothfuss |
| 4,043,504 A | 8/1977 | Hueil et al. |
| 4,144,890 A | 3/1979 | Hess |
| 4,164,225 A | 8/1979 | Johnson et al. |
| 4,168,703 A | 9/1979 | Kenigsberg |
| 4,177,818 A | 12/1979 | De Pedro |
| 4,210,148 A | 7/1980 | Stivala |
| 4,229,930 A | 10/1980 | Ostermaier |
| 4,235,238 A | 11/1980 | Ogiu et al. |
| 4,265,226 A | 5/1981 | Cassimally |
| 4,375,866 A | 3/1983 | Giersch et al. |
| 4,399,810 A | 8/1983 | Samuels et al. |
| 4,407,286 A | 10/1983 | Noiles et al. |
| 4,448,194 A | 5/1984 | DiGiovanni et al. |
| 4,471,781 A | 9/1984 | DiGiovanni et al. |
| 4,500,024 A | 2/1985 | DiGiovanni et al. |
| 4,506,670 A | 3/1985 | Crossley |
| 4,573,469 A | 3/1986 | Golden et al. |
| 4,585,153 A | 4/1986 | Failla et al. |
| 4,586,502 A | 5/1986 | Bedi et al. |
| 4,591,085 A | 5/1986 | DiGiovanni |
| 4,605,004 A | 8/1986 | DiGiovanni et al. |
| 4,606,345 A | 8/1986 | Dorband et al. |
| 4,607,638 A | 8/1986 | Crainich et al. |
| 4,627,437 A | 12/1986 | Bedi et al. |
| 4,635,637 A | 1/1987 | Schreiber |
| 4,649,938 A | 3/1987 | McArthur |
| 4,653,496 A | 3/1987 | Bundy et al. |
| 4,665,906 A | 5/1987 | Jervis |
| 4,669,473 A | 6/1987 | Richards et al. |
| 4,696,300 A | 9/1987 | Anderson |
| 4,705,040 A | 11/1987 | Mueller et al. |
| 4,724,840 A | 2/1988 | McVay et al. |
| 4,736,746 A | 4/1988 | Anderson |
| 4,741,336 A | 5/1988 | Failla et al. |
| 4,753,469 A | 6/1988 | Hiscott et al. |
| 4,809,695 A | 3/1989 | Gwathmey et al. |
| 4,841,888 A | 6/1989 | Mills et al. |
| 4,862,359 A | 8/1989 | Trivedi et al. |
| 4,880,015 A | 11/1989 | Nierman |
| 4,887,612 A | 12/1989 | Esser et al. |
| 4,890,615 A | 1/1990 | Caspari et al. |
| 4,935,027 A | 6/1990 | Yoon |
| 5,015,249 A | 5/1991 | Nakao |
| 5,037,021 A | 8/1991 | Mills et al. |
| 5,037,433 A | 8/1991 | Wilk et al. |
| 5,067,957 A | 11/1991 | Jervis |
| 5,076,285 A | 12/1991 | Hess et al. |
| 5,080,663 A | 1/1992 | Mills et al. |
| 5,088,979 A | 2/1992 | Filipi et al. |
| 5,147,373 A | 9/1992 | Ferzli |
| 5,174,487 A | 12/1992 | Rothfuss et al. |
| 5,190,546 A | 3/1993 | Jervis |
| 5,219,359 A | 6/1993 | McQuilkin et al. |
| 5,222,963 A | 6/1993 | Brinkerhoff et al. |
| 5,230,344 A | 7/1993 | Ozdamar et al. |
| 5,254,126 A | 10/1993 | Filipi et al. |
| 5,289,963 A | 3/1994 | McGarry et al. |
| 5,290,296 A | 3/1994 | Phillips |
| 5,309,923 A | 5/1994 | Leuchter et al. |
| 5,324,325 A | 6/1994 | Moaddeb |
| 5,331,969 A | 7/1994 | Silberstein |
| 5,336,263 A | 8/1994 | Ersek et al. |
| 5,346,504 A | 9/1994 | Ortiz et al. |
| 5,350,391 A | 9/1994 | Iacovelli |
| 5,354,311 A | 10/1994 | Kambin et al. |
| 5,356,416 A | 10/1994 | Chu et al. |
| 5,358,508 A | 10/1994 | Cobb |
| 5,364,408 A | 11/1994 | Gordon |
| 5,381,943 A | 1/1995 | Allen et al. |
| 5,383,260 A | 1/1995 | Deschenes et al. |
| D356,154 S | 3/1995 | Ferragamo |
| 5,395,030 A | 3/1995 | Kuramoto et al. |
| 5,395,367 A | 3/1995 | Wilk |
| 5,403,326 A * | 4/1995 | Harrison et al. ............ 606/139 |
| 5,433,721 A | 7/1995 | Hooven et al. |
| 5,437,266 A | 8/1995 | McPherson et al. |
| 5,441,507 A | 8/1995 | Wilk |
| 5,447,512 A | 9/1995 | Wilson et al. |
| 5,451,406 A | 9/1995 | Lawin et al. |
| 5,464,426 A | 11/1995 | Bonutti |
| 5,465,894 A | 11/1995 | Clark et al. |
| 5,470,337 A | 11/1995 | Moss |
| 5,485,952 A | 1/1996 | Fontayne |
| 5,486,189 A | 1/1996 | Mudry et al. |
| 5,496,331 A | 3/1996 | Xu et al. |
| 5,522,820 A | 6/1996 | Caspari et al. |
| 5,528,334 A | 6/1996 | Lee |
| 5,538,008 A | 7/1996 | Crowe et al. |
| 5,549,618 A | 8/1996 | Fleenor et al. |
| 5,558,665 A | 9/1996 | Kieturakis |
| 5,571,090 A | 11/1996 | Sherts |
| 5,571,116 A | 11/1996 | Bolanos et al. |
| 5,573,496 A | 11/1996 | McPherson et al. |
| 5,581,943 A | 12/1996 | Deren et al. |
| 5,588,581 A | 12/1996 | Conlon et al. |
| 5,597,378 A | 1/1997 | Jervis |
| 5,624,453 A | 4/1997 | Ahmed |
| 5,626,613 A | 5/1997 | Schmieding |
| 5,642,552 A | 7/1997 | Wang |
| 5,645,552 A | 7/1997 | Sherts |
| 5,662,683 A | 9/1997 | Kay |
| 5,665,096 A | 9/1997 | Yoon |
| 5,671,507 A | 9/1997 | Deschenes et al. |
| 5,674,230 A | 10/1997 | Tovey et al. |
| 5,676,674 A * | 10/1997 | Bolanos et al. ............ 606/139 |
| 5,697,940 A | 12/1997 | Chu et al. |
| 5,699,808 A | 12/1997 | John |
| 5,722,421 A | 3/1998 | Francese et al. |
| 5,725,524 A | 3/1998 | Mulier et al. |
| 5,728,109 A | 3/1998 | Schulze et al. |
| 5,735,861 A | 4/1998 | Peifer et al. |
| 5,741,280 A | 4/1998 | Fleenor |
| 5,749,898 A | 5/1998 | Schulze et al. |
| 5,787,897 A | 8/1998 | Kieturakis |
| 5,788,138 A | 8/1998 | Deschenes et al. |
| 5,792,153 A | 8/1998 | Swain et al. |
| 5,792,478 A | 8/1998 | Lawin et al. |
| 5,794,948 A | 8/1998 | Schmitt et al. |
| 5,797,927 A | 8/1998 | Yoon |
| 5,810,855 A | 9/1998 | Rayburn et al. |
| 5,810,882 A | 9/1998 | Bolduc et al. |
| 5,814,054 A | 9/1998 | Kortenbach et al. |
| 5,826,776 A | 10/1998 | Schulze et al. |
| 5,845,645 A | 12/1998 | Bonutti |
| 5,846,254 A | 12/1998 | Schulze et al. |

| Patent | Date | Name |
|---|---|---|
| 5,853,409 A | 12/1998 | Swanson et al. |
| 5,855,311 A | 1/1999 | Hamblin et al. |
| 5,887,594 A | 3/1999 | LoCicero, III |
| 5,893,592 A | 4/1999 | Schulze et al. |
| 5,897,562 A | 4/1999 | Bolanos et al. |
| 5,899,915 A | 5/1999 | Saadat |
| 5,901,895 A | 5/1999 | Heaton et al. |
| 5,954,731 A | 9/1999 | Yoon |
| 5,958,444 A | 9/1999 | Wallace et al. |
| 5,984,932 A | 11/1999 | Yoon |
| 5,993,466 A | 11/1999 | Yoon |
| 6,009,877 A | 1/2000 | Edwards |
| 6,051,003 A | 4/2000 | Chu et al. |
| 6,059,798 A | 5/2000 | Tolkoff |
| 6,067,990 A | 5/2000 | Kieturakis |
| 6,083,202 A | 7/2000 | Smith |
| 6,086,600 A | 7/2000 | Kortenbach |
| 6,086,603 A | 7/2000 | Termin et al. |
| 6,098,629 A | 8/2000 | Johnson et al. |
| 6,102,887 A | 8/2000 | Altman |
| 6,113,609 A | 9/2000 | Adams |
| 6,129,761 A | 10/2000 | Hubbell |
| RE36,974 E | 11/2000 | Bonutti |
| 6,152,935 A | 11/2000 | Kammerer et al. |
| 6,159,146 A | 12/2000 | El Gazayerli |
| 6,179,840 B1 | 1/2001 | Bowman |
| 6,221,084 B1 | 4/2001 | Fleenor |
| 6,238,335 B1 | 5/2001 | Silverman et al. |
| 6,254,642 B1 | 7/2001 | Taylor |
| 6,258,064 B1 | 7/2001 | Smith et al. |
| 6,267,285 B1 | 7/2001 | Raymond et al. |
| 6,312,437 B1 | 11/2001 | Kortenbach |
| 6,312,448 B1 | 11/2001 | Bonutti |
| 6,315,184 B1 | 11/2001 | Whitman |
| 6,325,503 B1 | 12/2001 | McCue, Jr. et al. |
| 6,352,503 B1 | 3/2002 | Matsui et al. |
| 6,387,104 B1 | 5/2002 | Pugsley, Jr. et al. |
| 6,443,973 B1 | 9/2002 | Whitman |
| 6,454,778 B2 | 9/2002 | Kortenbach |
| 6,461,366 B1 | 10/2002 | Seguin |
| 6,478,210 B2 | 11/2002 | Adams et al. |
| 6,494,888 B1 | 12/2002 | Laufer et al. |
| 6,506,196 B1 | 1/2003 | Laufer |
| 6,540,789 B1 | 4/2003 | Silverman et al. |
| 6,544,291 B2 | 4/2003 | Taylor |
| 6,544,503 B1 | 4/2003 | Vanderhoff et al. |
| 6,547,776 B1 | 4/2003 | Gaiser et al. |
| 6,548,501 B2 | 4/2003 | Hakkinen |
| 6,548,518 B2 | 4/2003 | Rubin et al. |
| 6,551,315 B2 | 4/2003 | Kortenbach et al. |
| 6,551,328 B2 | 4/2003 | Kortenbach |
| 6,552,045 B2 | 4/2003 | Rubin et al. |
| 6,552,046 B2 | 4/2003 | Druzgala et al. |
| 6,552,047 B2 | 4/2003 | Garvey et al. |
| 6,558,400 B2 | 5/2003 | Deem et al. |
| 6,558,429 B2 | 5/2003 | Taylor |
| 6,559,165 B1 | 5/2003 | Rubin et al. |
| 6,562,034 B2 | 5/2003 | Edwards et al. |
| 6,562,795 B2 | 5/2003 | Ashley et al. |
| 6,569,085 B2 | 5/2003 | Kortenbach et al. |
| 6,569,105 B1 | 5/2003 | Kortenbach et al. |
| 6,572,626 B1 | 6/2003 | Knodel et al. |
| 6,575,971 B2 | 6/2003 | Hauck et al. |
| 6,579,301 B1 | 6/2003 | Bales et al. |
| 6,589,238 B2 | 7/2003 | Edwards et al. |
| 6,591,137 B1 | 7/2003 | Fischell et al. |
| 6,591,838 B2 | 7/2003 | Durgin |
| 6,592,596 B1 | 7/2003 | Geitz |
| 6,592,609 B1 | 7/2003 | Bonutti |
| 6,595,909 B2 | 7/2003 | Silverman et al. |
| 6,595,910 B2 | 7/2003 | Silverman et al. |
| 6,604,004 B1 | 8/2003 | Zelickson et al. |
| 6,604,528 B1 | 8/2003 | Duncan |
| 6,605,078 B2 | 8/2003 | Adams |
| 6,609,140 B1 | 8/2003 | Greene |
| 6,613,047 B2 | 9/2003 | Edwards |
| 6,632,227 B2 | 10/2003 | Adams |
| 6,645,201 B1 | 11/2003 | Utley et al. |
| 6,652,545 B2 | 11/2003 | Shipp et al. |
| 6,660,301 B1 | 12/2003 | Vogel et al. |
| 6,663,639 B1 | 12/2003 | Laufer et al. |
| 6,666,848 B2 | 12/2003 | Stone |
| 6,669,713 B2 | 12/2003 | Adams |
| 6,673,058 B2 | 1/2004 | Snow |
| 6,673,070 B2 | 1/2004 | Edwards et al. |
| 6,692,507 B2 | 2/2004 | Pugsley et al. |
| 6,695,764 B2 | 2/2004 | Silverman et al. |
| 6,695,866 B1 | 2/2004 | Kuehn et al. |
| 6,699,243 B2 | 3/2004 | West et al. |
| 6,712,074 B2 | 3/2004 | Edwards et al. |
| 6,712,814 B2 | 3/2004 | Edwards et al. |
| 6,716,226 B2 | 4/2004 | Sixto, Jr. et al. |
| 6,716,233 B1 | 4/2004 | Whitman |
| 6,725,866 B2 | 4/2004 | Johnson et al. |
| 6,743,240 B2 | 6/2004 | Smith et al. |
| 6,773,440 B2 | 8/2004 | Gannoe et al. |
| 6,773,441 B1 | 8/2004 | Laufer et al. |
| 6,790,214 B2 | 9/2004 | Kraemer et al. |
| 6,790,237 B2 | 9/2004 | Stinson |
| 6,793,652 B1 | 9/2004 | Whitman et al. |
| 6,808,491 B2 | 10/2004 | Kortenbach et al. |
| 6,821,285 B2 | 11/2004 | Laufer et al. |
| 6,824,548 B2 | 11/2004 | Smith et al. |
| 6,835,200 B2 * | 12/2004 | Laufer et al. ................ 606/153 |
| 6,843,403 B2 | 1/2005 | Whitman |
| 6,843,794 B2 | 1/2005 | Sixto, Jr. et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,916,332 B2 | 7/2005 | Adams |
| 6,926,722 B2 | 8/2005 | Geitz |
| 6,945,979 B2 | 9/2005 | Kortenbach et al. |
| 6,971,395 B2 | 12/2005 | Edwards et al. |
| 6,981,941 B2 | 1/2006 | Whitman et al. |
| 6,986,737 B2 | 1/2006 | Suzuki et al. |
| 7,032,798 B2 | 4/2006 | Whitman et al. |
| 7,033,370 B2 | 4/2006 | Gordon et al. |
| 7,066,944 B2 | 6/2006 | Laufer et al. |
| 7,077,856 B2 | 7/2006 | Whitman |
| 7,087,073 B2 | 8/2006 | Bonutti |
| 7,153,314 B2 | 12/2006 | Laufer et al. |
| 2001/0049537 A1 | 12/2001 | Kortenbach |
| 2001/0056282 A1 | 12/2001 | Sonnenschein |
| 2002/0010418 A1 | 1/2002 | Lary et al. |
| 2002/0022851 A1 | 2/2002 | Kalloo et al. |
| 2002/0063143 A1 | 5/2002 | Adams et al. |
| 2002/0068945 A1 | 6/2002 | Sixto, Jr. et al. |
| 2002/0068946 A1 | 6/2002 | Kortenbach et al. |
| 2002/0078967 A1 | 6/2002 | Sixto, Jr. et al. |
| 2002/0082621 A1 | 6/2002 | Schurr et al. |
| 2002/0138086 A1 | 9/2002 | Sixto, Jr. et al. |
| 2002/0173786 A1 | 11/2002 | Kortenbach et al. |
| 2002/0193816 A1 | 12/2002 | Laufer et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2002/0198549 A1 | 12/2002 | Sixto et al. |
| 2003/0019905 A1 | 1/2003 | Adams et al. |
| 2003/0036679 A1 | 2/2003 | Kortenbach et al. |
| 2003/0065340 A1 | 4/2003 | Geitz |
| 2003/0065359 A1 | 4/2003 | Weller et al. |
| 2003/0068326 A1 | 4/2003 | Gevas et al. |
| 2003/0069280 A1 | 4/2003 | Koch et al. |

| | | | | | |
|---|---|---|---|---|---|
| 2003/0069646 A1 | 4/2003 | Stinson | GB | 2075829 | 11/1981 |
| 2003/0083241 A1 | 5/2003 | Young | JP | 61122852 | 6/1986 |
| 2003/0086968 A1 | 5/2003 | Gray | JP | 1151461 | 6/1989 |
| 2003/0092699 A1 | 5/2003 | Uchida et al. | JP | 05103241 A | 4/1993 |
| 2003/0130560 A1 | 7/2003 | Suzuki et al. | JP | 05323412 A | 12/1993 |
| 2003/0130561 A1 | 7/2003 | Suzuki et al. | JP | 08006102 A | 1/1996 |
| 2003/0135206 A1 | 7/2003 | Edwards et al. | JP | 2000254143 A | 9/2000 |
| 2003/0161887 A1 | 8/2003 | Klein | JP | 2001507972 T | 6/2001 |
| 2003/0163029 A1 | 8/2003 | Sonnenschein et al. | JP | 2003051982 A | 2/2003 |
| 2003/0167062 A1 | 9/2003 | Gambale et al. | JP | 2006311060 A | 11/2006 |
| 2003/0171645 A1 | 9/2003 | Silverman et al. | WO | WO-8911827 | 12/1989 |
| 2003/0181929 A1 | 9/2003 | Geitz | WO | WO-9627345 A2 | 9/1996 |
| 2003/0188755 A1 | 10/2003 | Milbocker | WO | WO-9803151 | 1/1998 |
| 2003/0191478 A1 | 10/2003 | Kortenbach et al. | WO | WO-9900059 | 1/1999 |
| 2003/0192558 A1 | 10/2003 | Durgin | WO | WO 99/22649 | 5/1999 |
| 2003/0192559 A1 | 10/2003 | Durgin | WO | WO-9922649 | 5/1999 |
| 2003/0195387 A1 | 10/2003 | Kortenbach et al. | WO | WO 99/60931 | 12/1999 |
| 2003/0195509 A1 | 10/2003 | Edwards et al. | WO | WO-9960931 | 12/1999 |
| 2003/0196670 A1 | 10/2003 | Durgin | WO | WO 00/35529 | 6/2000 |
| 2003/0199731 A1 | 10/2003 | Silverman et al. | WO | WO-0035529 | 6/2000 |
| 2003/0208209 A1 | 11/2003 | Gambale et al. | WO | WO 00/78227 | 12/2000 |
| 2003/0208211 A1 | 11/2003 | Kortenbach | WO | WO 00/78229 | 12/2000 |
| 2003/0216754 A1 | 11/2003 | Kraemer et al. | WO | WO-0078227 | 12/2000 |
| 2003/0220657 A1 | 11/2003 | Adams | WO | WO-0078229 | 12/2000 |
| 2003/0220660 A1 | 11/2003 | Kortenbach et al. | WO | WO-0185034 | 11/2001 |
| 2003/0236535 A1 | 12/2003 | Onuki et al. | WO | WO 02/24080 | 3/2002 |
| 2003/0236536 A1 | 12/2003 | Grigoryants et al. | WO | WO-0224080 | 3/2002 |
| 2004/0006336 A1 | 1/2004 | Swanson | WO | WO-0228289 | 4/2002 |
| 2004/0006351 A1 | 1/2004 | Gannoe et al. | WO | WO 02/40081 | 5/2002 |
| 2004/0010245 A1 | 1/2004 | Cerier et al. | WO | WO-0240081 | 5/2002 |
| 2004/0037887 A1 | 2/2004 | Bourne et al. | WO | WO 02/45603 | 6/2002 |
| 2004/0044364 A1 | 3/2004 | DeVries et al. | WO | WO-0245603 | 6/2002 |
| 2004/0059349 A1 | 3/2004 | Sixto et al. | WO | WO-0276541 | 10/2002 |
| 2004/0059350 A1 | 3/2004 | Gordon et al. | WO | WO-02076541 | 10/2002 |
| 2004/0059354 A1 | 3/2004 | Smith et al. | WO | WO 02/094341 | 11/2002 |
| 2004/0059358 A1 | 3/2004 | Kortenbach et al. | WO | WO-0294341 | 11/2002 |
| 2004/0082859 A1 | 4/2004 | Schaer | WO | WO-02094341 | 11/2002 |
| 2004/0082950 A1 | 4/2004 | Edwards et al. | WO | WO 03/000115 | 1/2003 |
| 2004/0082963 A1 | 4/2004 | Gannoe et al. | WO | WO 03/004087 | 1/2003 |
| 2004/0116948 A1 | 6/2004 | Sixto et al. | WO | WO 03/007796 | 1/2003 |
| 2004/0133238 A1 | 7/2004 | Cerier | WO | WO-03000115 | 1/2003 |
| 2004/0147943 A1 | 7/2004 | Kobayashi | WO | WO-03004087 | 1/2003 |
| 2004/0153107 A1 | 8/2004 | Kayan et al. | WO | WO-03007796 | 1/2003 |
| 2004/0162568 A1 | 8/2004 | Saadat et al. | WO | WO 03/015604 | 2/2003 |
| 2004/0176783 A1 | 9/2004 | Edoga et al. | WO | WO-03015604 | 2/2003 |
| 2004/0193184 A1 | 9/2004 | Laufer et al. | WO | WO-03030782 | 4/2003 |
| 2004/0193193 A1 | 9/2004 | Laufer et al. | WO | WO-03035649 | 5/2003 |
| 2004/0193194 A1 | 9/2004 | Laufer et al. | WO | WO-03037256 | 5/2003 |
| 2004/0194790 A1 | 10/2004 | Laufer et al. | WO | WO 03/053253 | 7/2003 |
| 2005/0033320 A1 | 2/2005 | McGuckin et al. | WO | WO-03053253 | 7/2003 |
| 2005/0033328 A1 | 2/2005 | Laufer et al. | WO | WO-03072196 | 9/2003 |
| 2005/0216036 A1 | 9/2005 | Nakao | WO | WO 03/082359 | 10/2003 |
| 2006/0025789 A1 | 2/2006 | Laufer et al. | WO | WO-03082359 | 10/2003 |
| 2009/0198254 A1 | 8/2009 | Laufer et al. | WO | WO 03/090633 | 11/2003 |
| | | | WO | WO 03/092498 | 11/2003 |
| | FOREIGN PATENT DOCUMENTS | | WO | WO 03/092509 | 11/2003 |
| | | | WO | WO 03/094800 | 11/2003 |
| EP | 0480428 | 4/1992 | WO | WO 03/096885 | 11/2003 |
| EP | 0 576 265 | 12/1993 | WO | WO-03090633 | 11/2003 |
| EP | 0576265 | 12/1993 | WO | WO-03092498 | 11/2003 |
| EP | 0 593 920 | 4/1994 | WO | WO-03092509 | 11/2003 |
| EP | 0593920 | 4/1994 | WO | WO-03094800 | 11/2003 |
| EP | 593920 A1 | 4/1994 | WO | WO-03096885 A2 | 11/2003 |
| EP | 0 646 356 | 4/1995 | WO | WO-03098885 | 11/2003 |
| EP | 0646356 | 4/1995 | WO | WO 03/099137 | 12/2003 |
| EP | 0 668 058 | 8/1995 | WO | WO 03/099139 | 12/2003 |
| EP | 9668058 | 8/1995 | WO | WO 03/099140 | 12/2003 |
| EP | 0 743 044 | 11/1996 | WO | WO 03/099376 | 12/2003 |
| EP | 0743044 | 11/1996 | WO | WO 03/105917 | 12/2003 |
| EP | 0 975 263 | 2/2000 | WO | WO 04/000129 | 12/2003 |
| EP | 0975263 | 2/2000 | WO | WO-03099137 | 12/2003 |
| FR | 2 768 324 | 3/1999 | WO | WO-03099139 | 12/2003 |
| FR | 2768324 | 3/1999 | WO | WO-03099140 | 12/2003 |

| | | |
|---|---|---|
| WO | WO-03099376 | 12/2003 |
| WO | WO-03105917 | 12/2003 |
| WO | WO-04000129 | 12/2003 |
| WO | WO-2004004542 | 1/2004 |
| WO | WO-2004004544 | 1/2004 |
| WO | WO-2004006990 | 1/2004 |
| WO | WO-2004019787 | 3/2004 |
| WO | WO-2004019788 | 3/2004 |
| WO | WO-2004021872 | 3/2004 |
| WO | WO-2004021873 | 3/2004 |
| WO | WO-2004021894 | 3/2004 |
| WO | WO-2004026348 | 4/2004 |
| WO | WO-2004026349 | 4/2004 |
| WO | WO-2004026350 | 4/2004 |
| WO | WO-2005086885 | 9/2005 |

OTHER PUBLICATIONS

Carvalho et al., "Fibrosis of Gastric Cardia After Endoscopic Sclerosis: Mechanism for Control of Experimental Reflux?" *The American Surgeon* (1990) 56:163-166.
Cecconello et al., Esophagogastric Anastomosis with Valvuloplasty: An Experimental Study *Int. Surg.* (1982) 67:121-124.
Collis, "An Operation for Hiatus Hernia with Short Esophagus," *J. Thorac. Surg.* (1957) 34:768-778.
Collis, "Surgical Control of Reflux in Hiatus Hernia," *Am. J. Surg.* (1968) 115:465-471.
Contractor et al., "Endoscopic Esophagitis and Gastroesophageal Flap Valve," *J. Clin. Gastroenterol.* (1999) 28:233-237.
Cuschieri et al., "Multicenter prospective evaluation of laparoscopic antireflux surgery," *Surg. Endosc.* (1993) 7:505-510.
DeMeester et al., "Nissen Fundoplication for Gastroesophageal Reflux Disease," *Annals of Surgery* (1986) 204:9-20.
Donahue et al., "Endoscopic sclerosis of the gastria cardia for prevention of experimental gastroesophageal reflux," *Gastrointest Endosc.* (1990) 36:253-256.
Falk et al., "Laparoscopic Fundoplication: A Preliminary Report of the Technique and Postoperative Care," *Aust. N.Z. J. Surg.* (1992) 62:969-972.
Hill et al., "The gastroesophageal flap valve: in vitro and in vivo observations," *Gastrointest Endosc.* (1996) 44:541-547.
Hill, "An Effective Operation for Hiatal Hernia: An Eight Year Appraisal," *Annals of Surgery* (1967) 166:681-692.
Hill, "Antireflux Surgery: A Surgeon's Look," *Gastroent. Clin. No. Amer.* (1990) 19:745-775.
Hill, "Intraoperative measurement of lower esophageal sphincter pressure," *J. Thorac. Cardiovasc. Surg.* (1978) 75:378-382.
Hill, "Myths of the esophagus," *J. Thorac. Cardiovasc. Surg.* (1989) 98:1-10.
Hill, "The Gastroesophageal Flap Valve," *J. Clin. Gastroenterol* (1999) 28:194-197.
Hill, "Surgery for Peptic Esophageal Stricture," 139-147.
Hinder et al., "The Surgical Option for Gastroesophageal Reflux Disease," Symposium on Gastroesophageal Reflux Disease *Am. J. Med.* (1997) 144S-148S.
Ismail et al., "Yield Pressure: A New Concept in the Evaluation of GERD?" *Br. J. Surg.* (1995) 82:943-947.
Jamieson et al., "Laparoscopic Nissen Fundoplication," *Annals of Surgery* (1994) 220:137-145.
Janssen et al., "Prospective randomized comparison of teres cardiopexy and Nissen fundoplication in the surgical therapy of gastro-oesophageal reflux disease," *Br. J. Surg.* (1993) 80:875-878.
Jennings et al., "A Novel Endoscopic Transgastric Fundoplication Procedure for Gastroesophageal Reflux: An Initial Animal Evaluation," *J. Laparoendosc. Surg.* (1992) 2:207-213.
Kadirkamanathan et al., "An ambulant porcine model of acid reflux used to evaluate endoscopic gastroplasty," *Gut* (1999) 44:782-788.
Kadirkamanathan et al., "Antireflux operations at flexible endoscopy using endoluminal stitching techniques: an experimental study," *Gastroint. Endosc.* (1996) 44:133-143.
Kahrilas, "Gastroesophageal Reflux Disease," *JAMA* (1996) 276:983-988.

Kraemer et al., "Laparoscopic Hill repair," *Gastrointestinal Endoscopy* (1994) 40:155-159.
Little, "Mechanisms of Action of Antireflux Surgery: Theory and Fact," *World J. Surg.* (1992) 16:320-325.
Mason et al., "A new intraluminal antigastroesophageal reflux procedure in baboons," *Gastroint. Endosc.* (1997) 45:283-290.
Mason et al., "Nissen Fundoplication Prevents Shortening of the Sphincter During Gastric Distention," *Arch. Surg.* (1997) 132:719-726.
McGouran et al., "A laser-induced scar at the cardia increases the yield pressure of the lower esophageal sphincter," *Gastrointest. Endosc.* (1990) 36:439-443.
McGouran et al., "Does measurement of yield pressure at the cardia during endoscopy provide information on the function of the lower oesophageal sphincter mechanism?" *Gut* (1988) 29:275-278.
McGouran et al., "Is yield pressure at the cardia increased by effective fundoplication?" *Gut* (1989) 30:1309-1312.
McKernan, "Laparoscopic repair of gastroesophageal reflux disease," *Surg Endosc* (1994) 8:851-856.
Nathanson et al., "Laparoscopic ligamentum teres (round ligament) cardiopexy," *Br. J. Surg.* (1991) 78:947-951.
Nissen, "Eine einlache Operation zur Beeinflussung der Refluxoesophagitis," *Journal Suise de Medecine* (1956) 590-592.
O'Connor et al.,"An experimental endoscopic technique for reversing gastroesophageal reflux in dogs by injecting inert material in the distal esophagus," *Gastro. Endosc.* (1984) 30:275-280.
O'Connor et al., "Endoscopic placement of collagen at the lower esophageal sphincter to inhibit gastroesophageal reflux: a pilot study of 10 medically intractable patients," *Gastroent. Endosc.* (1988) 34:106-112.
Pedinielli, "Traitement Chirurgical de la Hernie Hiatale par la Technique du Collet," *Ann. Chir.* (1964) 18:1461-1474.
Polk et al., "Hiatal Hernia and Esophagitis: A Survey of Indications for Operation and Technic and Results of Fundoplication,"*Ann. Surg.* (1971) 173:775-781.
Rampal et al., "Traitement des hernies hiatales et du reflux oesophagieu pa la cardio-pexie avec le ligament rond du foie," *Le Presse Medicale* (1967) 75:617-619.
Rich, "Simple GERD treatment offers new alternative," (www.medicalpost.com website) (Mar. 1999).
Rupp et al., "Endoscopic Antireflux Techniques: Endoluminal and Laparoscopic," *Exper. & Invest. Endosc.* (1994) 4:353-368.
Shafik, "Intraesophageal Polytef injection for the treatment of reflux esophagitis," *Surg. Endosc.* (1996) 10:329-331.
Singh et al., "Evaluation of the Endoscopic Suturing System in the Treatment of GERD," *DDW* (May 16-19, 1999).
Skinner et al., Surgical management of esophageal reflux and hiatus hernia, *J. of Thoracic & Cardiovas. Surg.* (1967) 53:33-54.
Slim et al., "Intraoperative Esophageal Manometry and Fundoplications: Prospective Study," *World J. Surg.* (1996) 20:55-59.
Starling et al., "Assessment of the Angelchik Prosthesis for Treatment of Symptomatic Esophageal Reflux," *World J. Surg.* (1987) 11:350-355.
Starling et al., "Treatment of Symptomatic Gastroesophageal Reflux Using the Angelchik™ Prosthesis," *Ann. Surg.* (1982) 686:690.
Thor et al., "Reappraisal of the Flap Valve Mechanism in the Gastroesophageal Junction," *Acta Chir. Scand.* (1987) 153:25-28.
Tocornal et al., "A mucosal flap valve mechanism to prevent gastroesophageal reflux and esophagitis," *Surgery* (1968) 64:519-523.
Wang et al., "A new anti-reflux procedure: cardiac oblique invagination," *Chung Hua Wai Ko Tsa Chih* (1995) 33 (2) 73-75 (English abstract).
Watson et al., "Comparison of anterior posterior and total fundoplication using a viscera model," *Diseases of the Esophagus* (1997) 10:110-114.
Westbrook et al., "Posterior Surgical Approaches to the Rectum," *Annals of Surgery* (1982) 195:677-691.
European Search Report dated Sep. 2, 2004 in EP 04076389.
Eurpoean Search Report mailed Jul. 10, 2007 in EP Application No. 07075291.
International Search Report dated Oct. 16, 2000.
International Search Report dated Oct. 22, 2003.

Boerema MD 'Hiatus Hernia: Repair by right-sided, subhepatic, anterior gastropexy' Surgery, 65:884-893 (1969).
Carvalho PJPC et al Fibrosis of gastric cardia after endoscopic sclerosis. Mechanism for control of experimental reflux? Am Surg Mar. 1990; 56(3):163-6.
DeMeester, MD et al 'Nissen Fundoplication for Gastroesophageal Reflux Disease' Annals of Surgery 204:9-20 (1986).
Hill et al 'Surgery for Peptic Esophageal Stricture' 139-147.
Hill et at 'The Esophagus, Medical and Surgical Management' WB Saunders Co. 135-8 (1988).
Hill LD 'Myths of the esophagus' J Thorac Cardiovasc Surg Jul. (1989)98(1):1-10.
Hill MD 'An Effective Operation for Hiatal Hernia: An Eight Year Appraisal' Annals of Surgery (1967) 166:681-692.
Kraemer, MD et al 'Laparascopic Hill repair' Gastrointestinal Endoscopy,vol. 40 No. 2 155-159 (1994).
Mason et al 'Nissen Fundoplication Prevents Shortening of the Sphincter During Gastric Distention' ARCH Surg., 132:719-726 (1997).
Skinner et al 'Surgical management of esophageal reflux and hiatus hernia' Journal of Thoracic and Cardiovascular Surgery (1967) vol. 53, No. 1 pp. 33-54.
Starling et al 'Assessment of the Angelchik Prosthesis for Treatment of Symptonatic Esophageal Reflux' World J. Surg. 11, 350-355 (1987).
Slim K et al., Intraoperative esophageal manometry and fundoplications: prospective study, World J Surg Jan. 1996;20(1):55-9.
Kahrilas, "Gastroesophageal Reflux Disease,"JAMA, 276:983-988 (1996).
Little, M.D., "Mechanisms of Action of Antireflux Surgery: Theory and Fact," World Journal of Surgery, 16:320-325 (1992).
McKernan, "Laparoscopic repair of gastroesophageal reflux disease," Surgical Endoscopy, 8:851-856 (1994).
Falk, et al., "Laparoscopic Fundoplication: A preliminary report of the technique and postoperative care," Aust. N.Z. J. Surgery, 62:969-972 (1992).
Kadirkamanathan SS et al., An ambulant procine model of acid reflux used to evaluate endoscopic gastroplasty. Gut Jun. 1999;44(6):782-8.
Mason RJ et al., A new intraluminal antigastroesphageal reflux procedure in baboons. Gastrointest Endosc Mar. 1997;45(3):283-90.
Hill LD et al., The gastroesophageal flap valve: in vitro and vivo observations. Gastrointest Endosc Nov. 1996;44(5):541-7.
Cuschieri, et al., "Multicenter prospective evaluation of laparoscopic antireflux surgery," Surgical Endoscopy, 7:505-510 (1993).
Hill LD, Intraoperative measurement of lower esophageal sphincter pressure. J. Thorac Cardiovasc Surg Mar. 1978;75(3):378-82.
Ismail T. et al., Yield pressure, anatomy of the cardia and gastro-oesophageal reflux. Br. J Surg Jul. 1995;82(7):943-7.
Kadirkamanathan SS et al., Antireflux operations at flexible endoscopy using enodluminal stitching techniques: an experimental study. Gastrointest Endosc Aug. 1996;44(2):133-43.
Digestive Disease Week, Orange County Convention Center, p. A-802; 314.
Contractor QQ et al., Endoscopic esphagitis and gastroesophageal flap valve. J Clin Gastroenterol Apr. 1999; 28 (3):233-7.
Cecconello, "Esophagogastric Anastomosis with Valvuloplasty: An Experimental Study," International Surgery, 67:121-124 1982.
Collis, M.D., "An Operation for Hiatus Hernia with Short Esophagus," The Journal of Thoracic Surgery, 34:768-778 (1957).
Collis, M.D., "Surgical Control of Reflux in Hiatus Hernia," The American Journal of Surgery, 115:465-471 (1968).
Donahue PE et al., Endoscopic sclerosis of the gastric cardia for prevention of experimental gastroesophageal reflux, Gastrointest. Endosc. May-Jun. 1990 36(3):253-6.
Hill LD and Kozarek RA, The gastroesophageal flap valve, J. Clin. Gastroenterol Apr. 1999 28(3): 194-7.
Hill LD et al., Antireflux surgery. A surgeon's look, Gastroenterol Clin. North Am. , Sep. 1990 19(3):745-75.
Hill LD, Myths of the esophagus, J. Thorac Cardiovasc. Surg. Jul. 1989 9S(1):1-10.

Hill, et al., "The Esophagus. Medical and Surgical Management," WB Saunders Co., 135-8 (1988).
Hinder, et al. "The Surgical Option for Gastroesophageal Reflux Disease," Symposium on Gastroesophageal Reflux Disease, Am. J. Med. 103:144S-148S (1997).
Ismail, et al., "Yield Pressure: A New Concept in the Evaluation of Gerd?," AJG, 91:616-617 (1996).
Jamieson, et al., "Laparoscopic Nissen Fundoplication," Annals of Surgery, 220:137-145 (1994).
Jamieson, et al., "The development of surgery for gastro-oesophageal reflux disease." Surgery of the Oesophagus, 233-245 (1988).
Janssen, et al., "Prospective randomized comparison of teres cardiopexy and Nissen fundoplication in the surgical therapy of gastro-oesophageal reflux disease." Br. J. Surg., 80:875-878 (1993).
Jennings, et al., "A Novel Endoscopic Transgastric Fundoplication Procedure for Gastroesophageal Reflux: An Initial Animal Evaluation," Journal of Laparoendoscopic Surgery, 2:207-213 (1992).
McGouran RC and Galloway JM, A laser-induced scar at the cardia increases the yield pressure of the lower esophageal sphicter, Gastrointest. Endosc. Sep.-Oct. 1990 36(5):439-43.
McGouran RC et al., Does measurement of yield pressure at the cardia during endoscopy provide information on the function of the lower oesophageal sphicter mechanism? Gut Mar. 1988 29(3):275-8.
Nathanson, et al., "Laparoscopic Ligamentum teres (round ligament) cardiopexy," Br. J. Surg., 78:947-951 (1991).
Issen, "Eine einfache Operation zur Beeinflussung der Refluxoesophagitis," Journal Suisee eMedecine, 590-592 (1956).
O'Connor KW and Lehman GA, Endoscopic placement of collagen at the lower esophageal sphicter to inhibit gastroesophageal reflux: a pilot study of 10 medically intractable patients. Gastrointest. Endosc. Mar.-Apr. 1988 34(2):106-12.
O'Connor KW et al., An experimental endoscopic technique for reversing gastroesophageal reflux in dogs by injecting inert material in the distal esophagus. Gastrointest. Endosc. Oct. 1984 30(5):275-80.
O'Connor, et al., "Endoscopic placement of collagen at the lower esophageal sphicter to inhibit gastroesophageal reflux: a pilot study of 10 medically intractable patients," Gastrointestinal Endoscopy, 34:106-112 (1988).
Pedinielli, "Traitement Chirurgical de la Herinie Hiatale Par La Technique du Collet," Ann. Chir., 18:1461-1474 (1964). (English Abstract).
Polk, et al., "Hiatol Hernia and Esophagitis: A survey of indications for operation and technic and results of fundoplication," Ann. Surg., 173:775-781 (1971).
Rampal, et al., "Technique Chirurgicale, Traitement des hernies hiatales et du reflux aesophagien par la cardio-pexie avec le ligament round de foie," La Presse Medicale, 75:617-619 (1967).
Rich, "Simple GERD Treatment Offers New Alternative" (www.medicalpost.com website), Mar. 1999.
Rupp TH and Lehman GA, Endoscopic antireflux techniques. Endoluminal and laparoscopic. Gastrointest. Endosc. Clin. N. Am. Apr. 1994 4(2):353-68.
Shafik A., Intraesophageal Polytef injection for the treatment of reflux esophagitis. Surg. Endosc. Mar. 1996 10(3):329-31.
Singh et al., "Evaluation of the Endoscopic Suturing System in the Treatment of the GERD," Conference Abstract for Plenary Session for Digestive Disease Week, p. 314 & A-802, May 16-19, 1999.
The Americal journal of gastroenterology, vol. 91, No. 3, 1996, p. 616-617.
Thor KBA et al., Reappraisal of the flap valve mechanism in the gastroesophageal junction. A study of a new valvuloplasty procedure in cadavers. Acta Chir Scand Jan. 1987 153(1):25-8.
Tocornal, M.D., et al., A mucosol flap valve mechanism to prevent gastroesophageal reflux and esophagitis, Surgery, 64:519-523 (1968).
Wang, et al., "A new anti-flux procedure: cardiac oblique invagination," Chung Hua Wai Ko Tsa Chih, Feb. 33 (2) 73-5 (1995). (English Abstract).
Watson, et al., "Comparison of anterior, posterior and total fundoplication using a viscera model," Diseases of the Esophagus, 10:110-114 (1997).

Westbrook, et al., "Posterior Surgical Approaches to the Rectum," *Annals of Surgery*, 195:677-691 (1982).

Bancewicz et al 'Yield Pressure, Anatomy of the cervix and Gastrooesphageal Reflux' The American Journal of Gastroenterology, vol. 91, No. 3, (1996) pp. 616-617.

Japanese Office Action for Application No. 2005-122394 dated May 12, 2009.

European Office Action dated Apr. 3, 2009 in EP07075291.0.

* cited by examiner

METHODS AND DEVICES FOR TISSUE RECONFIGURATION

This application claims the priority of U.S. provisional application Ser. No. 60/306,652, filed Jul. 18, 2001, which is hereby incorporated by reference in its entirety.

This application is a continuation-in-part of copending application U.S. Ser. No. 09/859,579, filed May 18, 2001 now U.S. Pat. No. 6,821,285, entitled TISSUE RECONFIGURATION, which is a continuation-in-part of application U.S. Ser. No. 09/574,424, filed May 19, 2000 now U.S. Pat. No. 6,494,888, entitled TISSUE RECONFIGURATION, which is a continuation-in-part of application U.S. Ser. No. 09/520,273, filed Mar. 7, 2000 now U.S. Pat. No. 6,663,639, entitled METHODS AND DEVICES FOR TISSUE RECONFIGURATION, and application U.S. Ser. No. 09/519,945, filed Mar. 7, 2000 U.S. Pat. No. 6,506,196, entitled DEVICE AND METHOD FOR CORRECTION OF A PAINFUL BODY DEFECT, which claim priority from provisional application. U.S. Ser. No. 60/140,492, filed Jun. 22, 1999, entitled STOMACH ELEVATOR METHOD AND DEVICE, all hereby incorporated by reference in their entirety.

BACKGROUND OF THE INVENTION

Brief Description of the Related Art

This invention relates to devices and methods for treating gastroesophageal reflux disease, and more particularly, the invention relates to a minimally invasive device and method for creating and fixating a fold of tissue at or near the junction of the esophagus and the stomach.

Gastroesophageal reflux disease (GERD) is a common upper-intestinal disorder in which contents of the stomach flow inappropriately from the stomach into the esophagus. Backflow of gastric contents into the esophagus results when gastric pressure is sufficient to overcome the resistance to flow that normally exists at the gastroesophageal junction (GEJ), or when gravity acting on the contents is sufficient to cause flow through the GEJ. Medication, open surgical procedures, laparoscopic surgical procedures, and endoscopic techniques are known for treating GERD.

SUMMARY OF THE INVENTION

According to one aspect of the invention, a medical instrument includes moveable arms configured for fixating the wall of the stomach to the wall of the esophagus for the treatment of GERD. In one embodiment, the instrument includes a proximal end, a shaft, a retroflexing portion, movable arms, a retractor, and an implant. The movable arms are oriented with respect to the retroflexing portion in a position that allows the stomach wall to be folded against the esophagus wall. In one such embodiment of this instrument the movable arms open and close in the same plane within which the retroflexing portion moves. This configuration is in contrast to certain embodiments of the medical instrument described in the U.S. patent application Ser. No. 09/859,579, entitled "TISSUE RECONFIGURATION," filed 18 May 2001, in which the moveable arms are oriented in a plane rotated 90 degrees from the plane in which the retroflexing portion moves. The mechanism of operation of the medical instrument of the current invention is as is disclosed in the patent applications incorporated by reference and listed above.

According to another aspect of the invention, a method of treatment includes fixating the wall of the stomach to the wall of the esophagus for the treatment of GERD.

According to another aspect of the invention, a method includes advancing an apparatus having an elongated member transorally into the stomach. The apparatus includes a distal end effector having first and second members configured to engage tissue. The first and second members are movable relatively toward one another generally in a first plane. The method includes moving the distal end effector relative to the elongated member in the first plane such that the distal end effector is retroflexed out of alignment with the elongated member to position the first and second members for engagement with the tissue. At least one of the first and second members carries a fixation device for fixing engaged portions of tissue together.

Embodiments of this aspect of the invention may include one or more of the following features. The method includes engaging tissue by moving the first and second members relatively toward one another generally in the first plane. Moving the first and second members engages a first tissue section with a first securing part of the fixation device and a second tissue section with a second securing part of the fixation device. The method includes piercing the tissue with a third member of the distal end effector prior to engaging the tissue with the first and second members.

According to another aspect of the invention, a method of treatment includes advancing a flexible shaft to a treatment site, piercing tissue with a member located at a distal portion of the shaft, and stabilizing tissue being pierced by contacting a surface of the tissue with a tissue stabilizer biased in a distal direction such that as the tissue piercing member enters tissue, the tissue stabilizer is urged against the surface of the tissue.

According to another aspect of the invention, a medical instrument for reconfiguring tissue includes a flexible shaft defining a lumen housing actuating controls, and a distal actuating assembly. The distal actuating assembly includes a sealing portion configured to substantially seal the shaft lumen from contact with bodily fluids, and a tissue manipulator located distal of the sealing portion. The actuating member is coupled to the tissue manipulator such that the tissue manipulator is actuatable to deploy an implant located distal of the sealing portion.

BRIEF DESCRIPTION OF THE DRAWINGS

The invention will now be described in greater detail with reference to the preferred embodiment illustrated in the accompanying drawings, in which like elements bear like reference numerals, and wherein.

DETAILED DESCRIPTION OF THE PREFERRED EMBODIMENT

Figure 1:
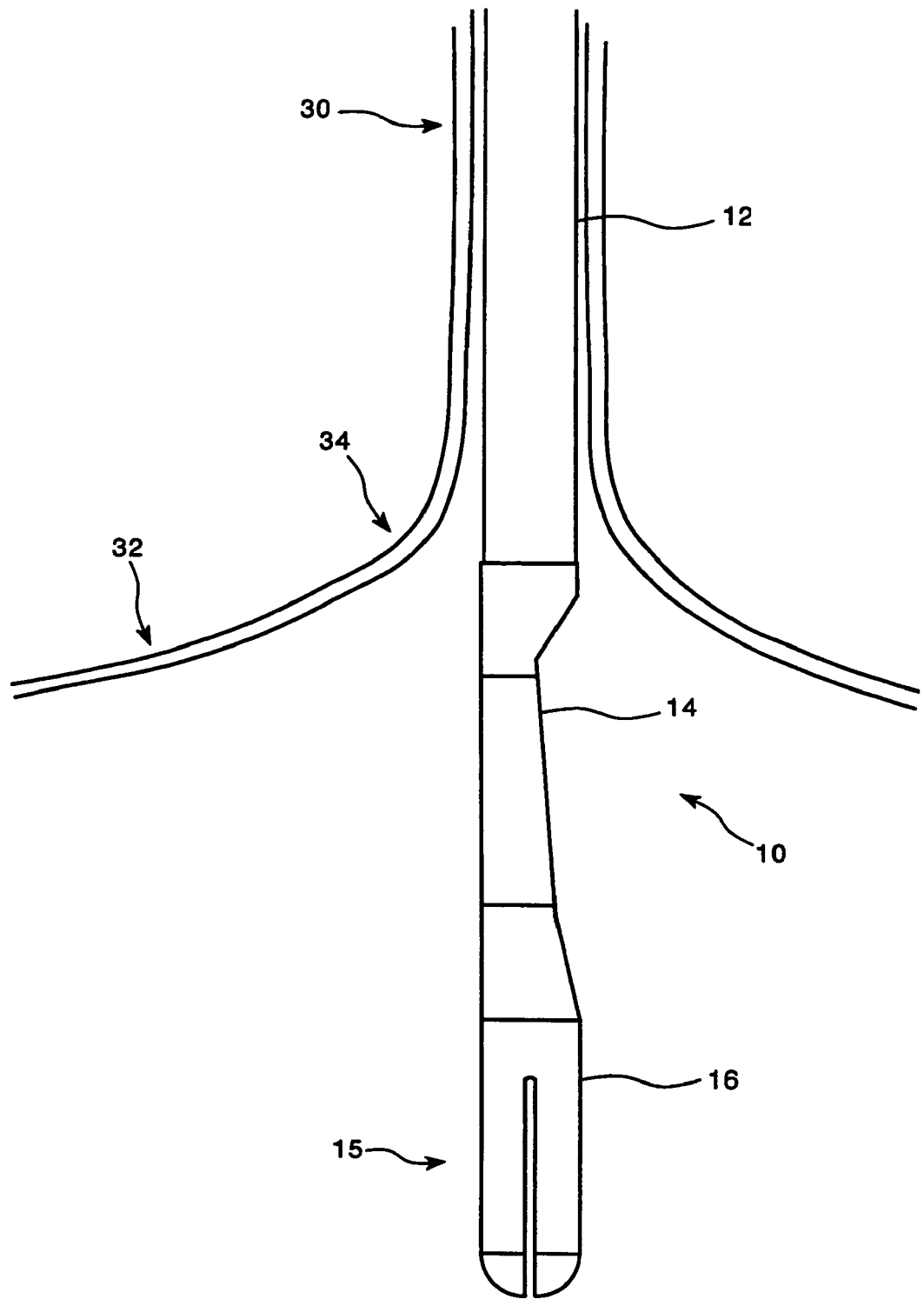
FIG. 1 is a side cross sectional view of a portion of an esophagus and a portion of a stomach, and a side view of an instrument in place in the esophagus and stomach.

In one aspect, the present invention provides endoscopic methods for reconfiguring tissue within a hollow body organ. The method of the invention may be applied to any hollow organ, as defined below. In a broad sense, the methods include at least the steps of engaging a portion of the inner surface of the hollow organ to be reconfigured, manipulating the engaged portion of tissue to create the reconfiguration, and fixing the manipulated tissue to retain the reconfiguration achieved in the manipulation. The methods may also include the step of endoscopic visualization during all or part of the procedure. Details of the shapes that can be assumed by the reconfigured tissue are discussed below.

As used herein, "endoscopic method" refers to a technique for performing a medical procedure on a subject in which access to the tissue to be treated is gained via an endoluminal approach. In a preferred embodiment an endoscopic method is performed without a contemporaneous invasive approach involving a surgical incision to gain access to the area of treatment. This preferred embodiment embraces use of at least one intravenous catheter for the administration of crystalloid or colloid fluids or medication to the subject, but does not require placement through the abdominal wall of an intraabdominal set of trocars, laparoscope, or the like.

The methods of the invention also contemplate gaining access to the interior of a subject's stomach via a gastrotomy or gastrostomy. Such methods, which retain the feature of involving minimally invasive access to tissue to be reconfigured, may be of particular value in situations where access via the esophagus is not possible due to distortion or disruption of normal oropharyngeal or proximal esophageal anatomy. Such methods may also be of particular value when a gastrotomy or gastrostomy is present for other medical reasons, such as for enteral feeding, for example.

As used herein, "hollow organ" refers to an organ of a subject's body which depends for its principal function upon its ability to receive and/or act as a conduit for liquid contents. A hollow organ typically is in fluid communication with another hollow organ and/or with the outside of the body. Many organs of the gastrointestinal and genitourinary tracts are classified as hollow viscus organs. These include stomach, gall bladder, uterus, and bladder. Other hollow organs which act more as fluid passageways include esophagus, small and large intestines, hepatic ducts, cystic duct, common bile duct, pancreatic duct, heart, veins, arteries, vagina, uterine (i.e., Fallopian) tubes, ureters, and urethra.

Endoscopic visualization can be used for all, at least a part, or none of the procedure. In certain preferred embodiments of the invention, the method is performed in conjunction with endoscopic visualization of at least the engaged portion of tissue. Typically, a first step in the method of the invention includes advancing an endoscope into the interior or lumen of a first hollow organ. Preferably, but not necessarily, endoscope is advanced into the interior of first hollow organ by way of a lumen of a second hollow organ in fluid communication with the first hollow organ.

Endoscopes are well known in the art. Viewing endoscopic instruments typically are equipped with a lighting element and a viewing element enabling an operator to view the interior of the accessed body cavity. Viewing endoscopic instruments often also include at least one fluid channel suitable for introducing and/or withdrawing a fluid, gas, or medicament, and a working channel suitable to accommodate a remotely operated surgical tool such as a needle, a grasper, a biopsy device, a brush, an electrocautery electrode, and the like. Acceptable viewing elements include fiberoptic-assisted direct visualization, television array, and video array endoscopes. Endoscope can be introduced into lumen of the first hollow organ for at least one aspect of the procedure and removed for at least one other aspect of the procedure. Accordingly, a viewing endoscope can be introduced, removed, and reintroduced for any one or for any combination of steps of the method of the invention.

For the purposes of the invention, a viewing endoscope can be an instrument separate from any other instrument employed in the practice of the method of the invention. Alternatively, a viewing endoscope can work cooperatively with at least one other instrument used in the practice of the invention by, for example, the at least one other instrument's cooperatively positioning the endoscope. In other embodiments, a viewing endoscope can be incorporated into a tissue engaging device, at least a portion of a tissue fixing device, or part of a combined tissue engaging and tissue securing device.

In other embodiments of the invention, the method is performed at least in part with non-endoscopic visualization of the tissue engaged. Non-endoscopic methods of visualization include techniques well known in the art, such as, without limitation, fluoroscopy, either with or without the use of a suitable radiographic contrast agent, and ultrasound. In some embodiments the procedure can be performed without any endoscopic visualization.

As used herein, the term "engaging" refers to an act of reversibly penetrating, gripping, tweezing, holding, pressing, clamping, sucking, or otherwise contacting a tissue in a mechanical fashion so as to establish a physical connection with the tissue. In certain preferred embodiments of the invention the engagement of tissue occurs reversibly and essentially atraumatically.

For example, in a most preferred embodiment the tissue engagement device includes a novel corkscrew-type element, described below. Even though the sharpened end of the spiral corkscrew-type element pierces in order to engage tissue, when the spiral is removed by unscrewing it from tissue, it leaves a single discrete point of penetration which self-seals in the extremely pliable tissue lining of the stomach, much as does a hole made in the same tissue with a hypodermic needle.

The tissue engaging device in some embodiments can be a separate instrument unto itself. In other embodiments the tissue engaging device can be used in combination with another endoscopic instrument. In yet other embodiments the tissue engaging device can be an element of a combination endoscopic instrument. In a preferred embodiment the tissue engaging device is an element of an endoscopic instrument which also incorporates a tissue securing device (see below).

In certain preferred embodiments the engaged portion involves just the inner lining of the first hollow organ. For example the engaged portion can involve only the mucosa in a stomach. In other embodiments the engaged portion can involve the inner lining and at least one additional tissue layer of first hollow organ. Again with reference to the stomach, the reconfigured portion can involve the mucosa and at least one layer of muscular wall, up to and including the full thickness of the stomach wall.

In certain preferred embodiments the tissue engaging device can engage tissue in a reversible and essentially atraumatic manner. Engagement of tissue in such embodiments is effective for performing subsequent steps of the method but also allows release of engaged tissue in a manner which causes little or no disruption of tissue integrity.

For example, in a most preferred embodiment the tissue engagement device includes a novel corkscrew-type element, described below. Even though the sharpened end of the spiral corkscrew-type element pierces in order to engage tissue, when the spiral is removed by unscrewing it from tissue, it leaves a single discrete point of penetration which self-seals in the extremely pliable tissue lining of the stomach, much as does a hole made in the same tissue with a hypodermic needle.

In yet other embodiments the tissue engaging device can be a known clamping device. Examples of suitable endoscopic clamping devices are well known in the art, including, without limitation, endoscopic alligator grasping forceps, forked jaw grasping forceps, rat tooth grasping forceps, three-prong grasping forceps, tripod grasping forceps, fenestrated cup forceps, and ellipsoid fenestrated forceps. As used herein, each such endoscopic clamping device is considered to engage a single portion of tissue, i.e., all tissue contacted by the various jaws of a single clamping device is considered as a single point of tissue engagement.

In other preferred embodiments the tissue engaging device can be a novel suction device, as described below. Tissue is engaged when contacted with suction and released atraumatically when the suction is broken at a point other than the point of tissue engagement.

According to the above embodiments, the tissue engaging device can engage tissue for the purposes of side-to-side manipulation, twisting, pushing, or retracting tissue. In yet another embodiment a tissue engaging device may be the sharpened end of, for example, at least one leg of a surgical staple. According to this embodiment, the tissue engaging device can engage tissue for the purposes of side-to-side manipulation, twisting, or pushing, but not for retracting tissue.

In a preferred embodiment a tissue engaging device may be incorporated into a tissue manipulating device. In this embodiment, the elongate portion of the tissue engaging device is further structured to permit manipulation of tissue engaged by atraumatic grasping, suction, or piercing as above. In a most preferred embodiment, as discussed below, a novel single instrument incorporating both a tissue engaging and tissue manipulation device is structured to permit independent engagement of tissue at two or more points, and to permit manipulation of at least two points of tissue with respect to each other in any direction in three-dimensional space. The two or more independent points of tissue engagement typically are separated by at least 1 cm prior to tissue engagement.

In a preferred embodiment, an endoscopic tissue engaging device is advanced into lumen of first hollow organ, preferably via a lumen of second hollow organ. The first hollow organ is shown as a stomach and second hollow organ is shown as an esophagus in fluid communication with organ. The related portion of inner surface of first hollow organ is engaged with endoscopic tissue engaging device, which is described below.

In one preferred embodiment engaging is accomplished by gripping tissue with a known jawed forceps device. The device includes opposed jaws and/or having teeth or the like. The engaging force must be sufficient to maintain physical connection with the engaged portion of tissue when a tissue-deforming torque, push, or retraction is applied to the engaged tissue via the tissue engaging device, while at the same time the force distribution is sufficient to avoid piercing, tearing, or cutting the surface of the engaged portion.

In certain preferred embodiments of the invention the engagement involves simultaneous engagement of at least two distinct sites. This effect can be achieved by simultaneously applying at least two tissue engagement devices, e.g., two separate endoscopic forceps clamps, or applying a single tissue engagement device designed to engage tissue simultaneously at distinct sites.

Release of the engaged portion is necessary in order to remove the engaging device from the hollow organ of the subject after having engaged the tissue. The engaged portion typically will participate in the reconfigured portion; i.e., the reconfigured tissue will typically comprise in some aspect, be it at a basal, apical, or intermediate position relative to the reconfigured portion as a whole, the tissue actually engaged by the engaging device in the course of reconfiguring.

In a subsequent step of the invention, the engaged portion of inner surface of first hollow organ is manipulated to reconfigure at least a portion of first hollow organ. The inner surface of first organ is manipulated by device to create a reconfigured portion. In the manipulating step a physical force is applied by device to the engaged portion of tissue of inner surface effective for pushing, pulling, twisting, rolling, folding, gathering, or otherwise displacing tissue from its original position and/or configuration prior to application of such force. In preferred embodiments, tissue in adjacent continuity with the portion actually engaged will undergo at least some degree of physical deformation from its original conformation in proportion to the magnitude and direction of force applied to the engaged portion. Manipulation of engaged tissue may be used to create an invagination, an evagination, or a combination of invagination and evagination of at least inner layer of first hollow organ.

In one embodiment of this aspect of the invention, manipulation of the engaged portion of inner surface of first hollow organ is achieved by applying traction force or torquing force to create reconfigured portion, which is an invagination. Traction force can be linear, such as achieved by pulling. Alternatively, traction force can be nonlinear, such as can be achieved by winding engaging tissue onto a spool.

As used herein, "invaginated portion" or "invagination" refers to a region of tissue displaced toward the interior cavity of the hollow organ as a combined result of engaging and manipulating. The particular shape assumed by the invaginated portion will depend on factors including the geometry of the engaged portion, the anatomy of the engaged organ, the plasticity of the segment of the organ engaged, and the direction and magnitude of the force applied.

According to an embodiment of this aspect of the invention, manipulation can entail bringing into apposition at least two points of tissue which are independently engaged by at least one tissue engaging device.

According to yet another embodiment of this aspect of the invention, combinations of tissue invaginations are created. Thus for example a flap and a bulge can be created in combination. Other embodiments include, without limitation, at least two flaps; at least two bulges; at least two rolls; a roll and a bulge; etc. Combinations of tissue invaginations can be created essentially contemporaneously or consecutively.

According to yet another embodiment of this aspect of the invention, manipulation of the engaged portion of the inner surface of the first hollow organ can be achieved by applying a leading or pushing force so as to create, from within, an outward protrusion of the first hollow organ (not shown). According to this method reconfigured portion is an evagination rather than an invagination. An evaginated portion can assume any of a number of shapes as viewed from the exterior of the hollow organ, including, without limitation, a bulge, a lump, a ridge, a flap, a fold, a tube, a horn, and a cone. As also viewed from the exterior of the hollow organ, a tissue evagination can be smooth, dimpled, or furrowed. The circumference at its base can be irregular or it can be substantially regular, e.g., substantially elliptical, substantially circular, substantially triangular, or substantially rectangular. The method also contemplates the formation of a plurality of evaginations, which may be created either simultaneously or sequentially. At least one evagination can be combined with at least one invagination.

In some embodiments reconfigured portion involves just the inner lining of the first hollow organ. For example reconfigured portion can involve only the mucosa in a stomach. In other embodiments reconfigured portion can involve the inner lining and at least one additional tissue layer of first hollow organ. Again with reference to the stomach, the reconfigured portion can involve the mucosa and at least one layer of muscular wall, up to and including the full thickness of the stomach wall.

After the manipulating step, a subsequent step involves permanently securing the reconfigured portion of the first hollow organ to effect a substantially permanent retention of the shape of the reconfigured portion. While the reconfigured portion of the organ is maintained under control of the operator through the manipulating force applied to the engaged portion of tissue via the tissue engaging device, the operator causes a distal effector end of a tissue securing device to come into contact with the reconfigured portion. The distal effector end of the tissue securing device includes at least one biocompatible tissue fixation device and is structured for application of at least one biocompatible tissue fixation device into the reconfigured portion. The tissue securing device is advanced into the lumen of the first hollow organ before, along with, or after the tissue engaging device; thereafter, the tissue securing device is actuated to apply at least one biocompatible tissue fixation device to permanently secure or fix the shape of reconfigured portion.

The tissue securing device in some embodiments can be a separate instrument unto itself. In other embodiments the tissue securing device can be used in combination with another endoscopic instrument. In yet other embodiments the tissue securing device can be an element of a combination endoscopic instrument. In a preferred embodiment, the tissue securing device is an element of an endoscopic tissue shaping instrument which also incorporates a tissue engaging device.

In certain embodiments, the tissue fixation device penetrates only an internal layer of first hollow organ. The internal layer can be, for example, the mucosa lining the interior of the stomach. Alternatively, the tissue fixation device penetrates both internal and at least one additional layer of first hollow organ. The at least one additional layer can be, for example, a muscle layer of the stomach wall. The combined inner layer and at least one additional layer constitute either a partial-thickness layer or a full-thickness layer. The securing step of this method includes, for example, fixation of an inner layer to a partial-thickness layer. This step also includes, for example, fixation of an inner layer to a full-thickness layer. In certain other methods, in the securing step, the tissue fixation device penetrates (1) a partial-thickness layer and (2) a full-thickness layer, or two full-thickness layers of the first hollow organ 10. This latter securing step fixes, for example, a full-thickness invagination in which two or more distinct regions of the exterior surface of the first hollow organ are brought into apposition (not shown).

Bench testing was conducted using an excised pig stomach and attached esophagus to demonstrate the principle of creating a bulge to prevent gastroesophageal reflux. The duodenum was clamped, an incision was made in the greater curvature of the stomach, and the stomach was inverted and filled with water. Water was observed to flow under the force of gravity from the stomach to the esophagus in a steady stream. A bulge was made in the wall of the stomach within one inch of the opening of the esophagus into the stomach. The bulge was fixed in place with a staple. The stomach was then refilled with water. No water was observed to flow under the force of gravity from the stomach to the esophagus following this procedure. A one-half inch diameter cylinder was passed through the esophagus and opening of the esophagus into the stomach both before and after creation of the bulge, indicating that the bulge did not close the lumen of the opening of the esophagus into the stomach.

The device consists of an instrument 10 with a proximal end (not shown), a shaft 12, a retroflexing portion 14, and a distal end effector 15 including movable arms 16, a retractor 20, and an implant 22. The function of the instrument is controlled by the user by controls at the proximal end, as is disclosed in the referenced patent applications. The device and method of the present invention will be illustrated using the accompanying drawings.

Figure 2:
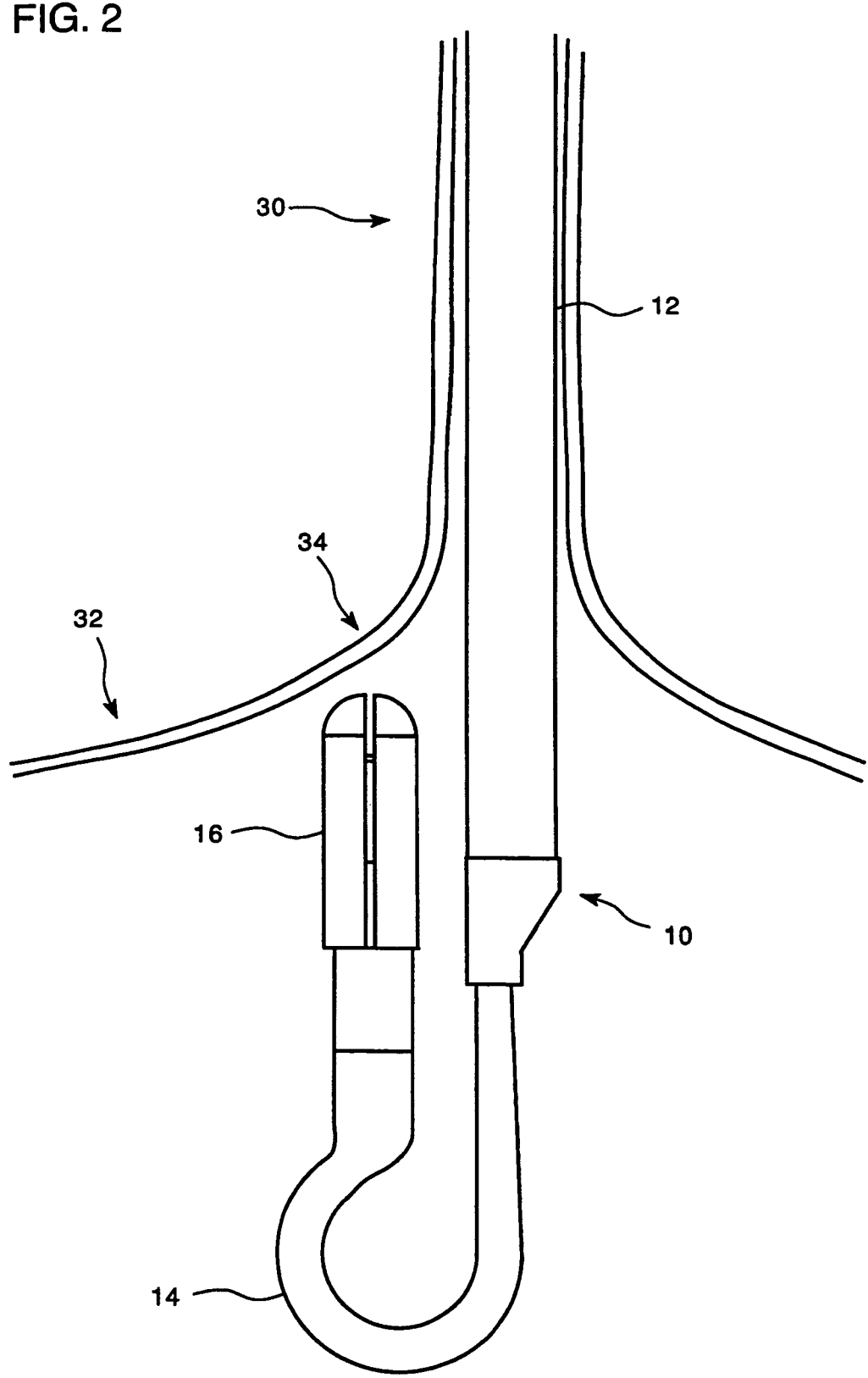
FIG. 2 is a side cross sectional view of a portion of the esophagus and a portion of the stomach, and a side view of the instrument in place in the esophagus and stomach, showing the instrument in a retroflexed position.

FIG. 1 shows the instrument 10 in place in the esophagus 30 and the stomach 32. The instrument is in a straight configuration, which is the configuration in which it is inserted into the esophagus and stomach FIG. 2 shows the instrument 10 in place in the esophagus 30 and the stomach 32, with the instrument 10 in a retroflexed position. Retroflexion of retroflexing portion 14 is accomplished as disclosed in the referenced patent applications. In this position, the distal end of the movable arms 16 of distal end effector 15 is located near the junction 34 of the esophagus 30 and the stomach 32.

Figure 3:
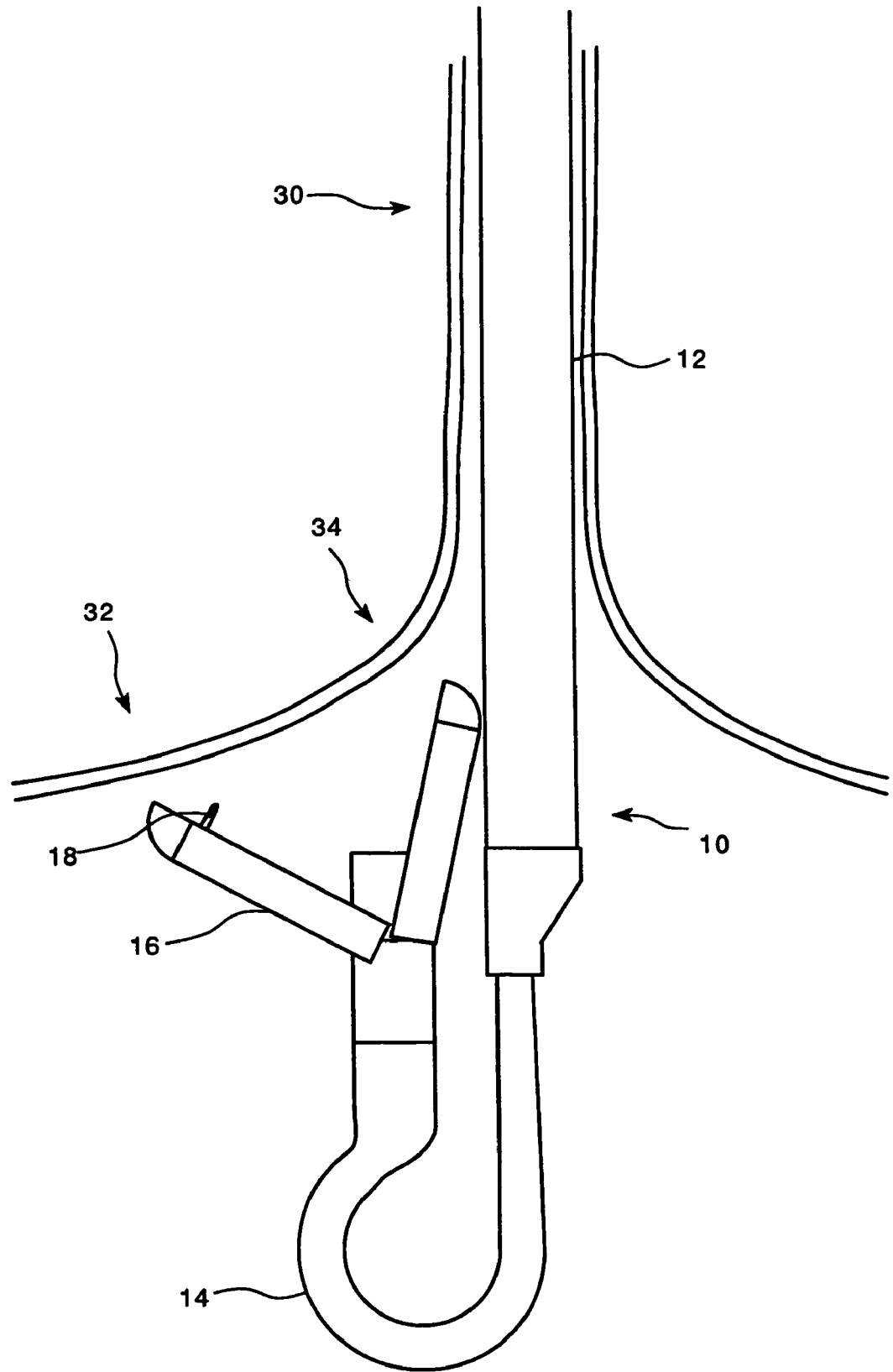
FIG. 3 is a side cross sectional view of a portion of the esophagus and a portion of the stomach, and a side view of the instrument in place in the esophagus and stomach, showing the movable arms open.
Figure 7:
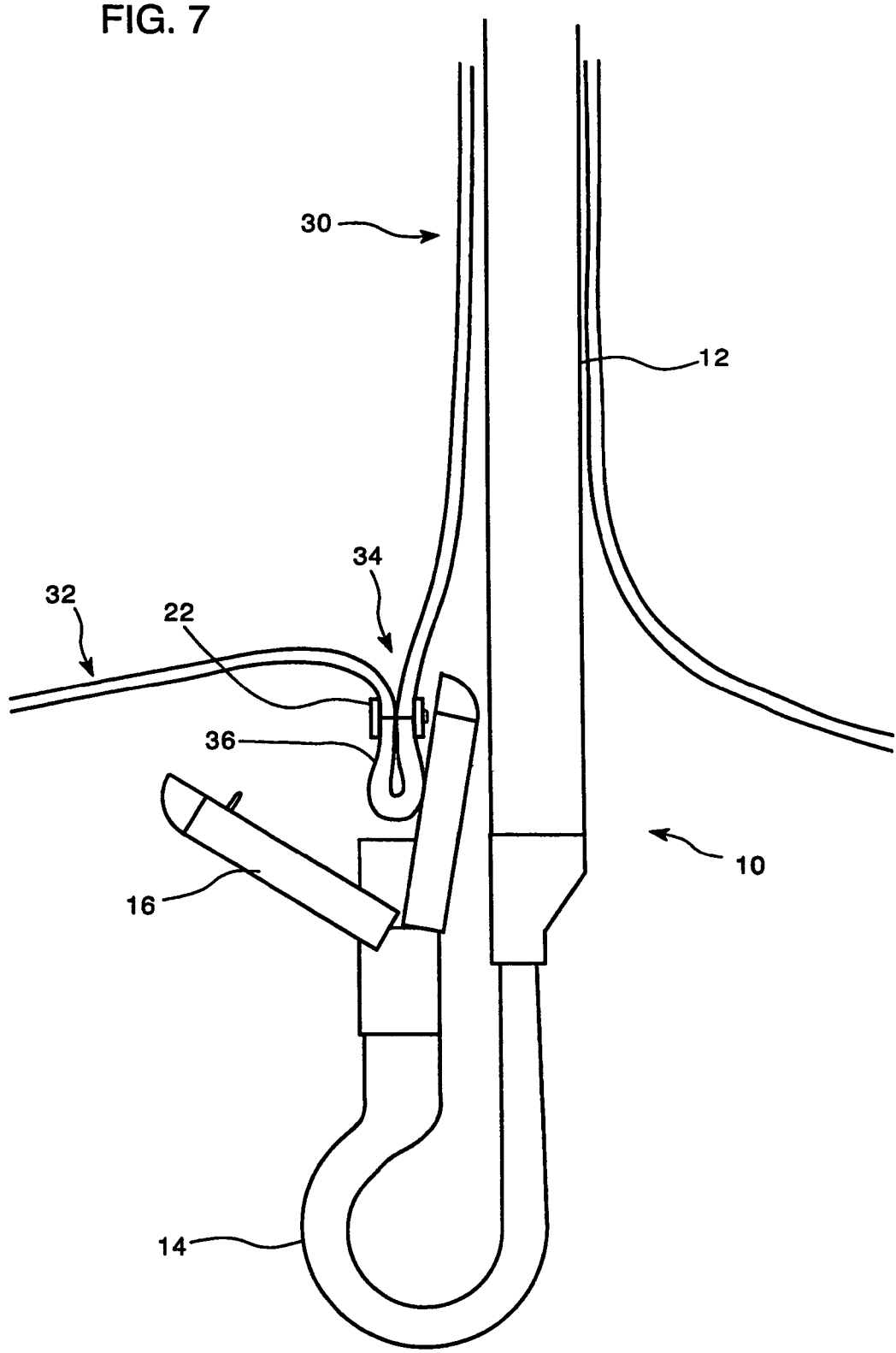
FIG. 7 is a side cross sectional view of a portion of the esophagus and a portion of the stomach, and a side view of the instrument in place in the esophagus and stomach, showing the movable arms open and an implant fixating the tissue fold.

FIG. 3 shows the instrument 10 in place in the esophagus 30 and the stomach 32, with the instrument 10 in a retroflexed position and the movable arms 16 in an open position revealing a portion 18 of an implant 22 (FIG. 7). It is important to note that the moveable arms 16 are oriented relative to the retroflexing portion 14 to grasp the tissue at the junction 34 of the esophagus 30 and the stomach 32. The movable arms 16 open and close in the same plane within which the retroflexing portion 14 moves. The actuating mechanism used to open movable arms 16 is substantially the same as the mechanisms used to actuate the medical instruments described in the U.S. patent application Ser. No. 09/859,579, entitled "TISSUE RECONFIGURATION," filed 18 May 2001, with the movable arms rotated 90.degree. with respect to the configuration of the published application such that the arms 16 open and close in the same plane within which the retroflexing portion 14 moves.

Figure 4:
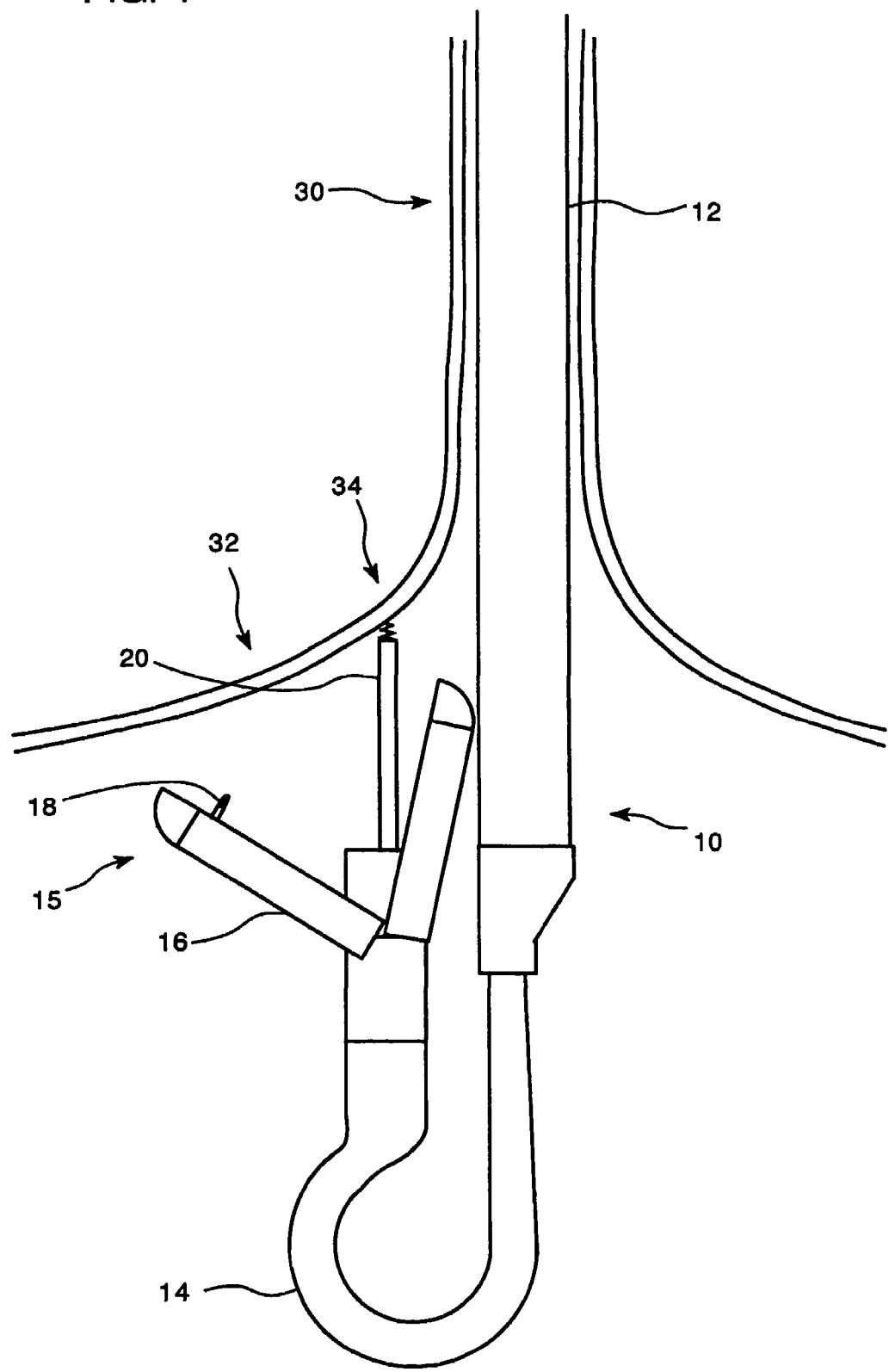
FIG. 4 is a side cross sectional view of a portion of the esophagus and a portion of the stomach, and a side view of the instrument in place in the esophagus and stomach, showing a retractor engaging tissue.

FIG. 4 shows the instrument 10 in place in the esophagus 30 and the stomach 32, with the instrument 10 in a retroflexed position, the movable arms 16 in an open position, and the retractor 20 engaged with the tissue at or near the junction 34 of the esophagus 30 and the stomach 32. Engagement of the retractor 20 with the tissue at or near the junction 34 is accomplished as is disclosed in the referenced patent applications.

Figure 5:
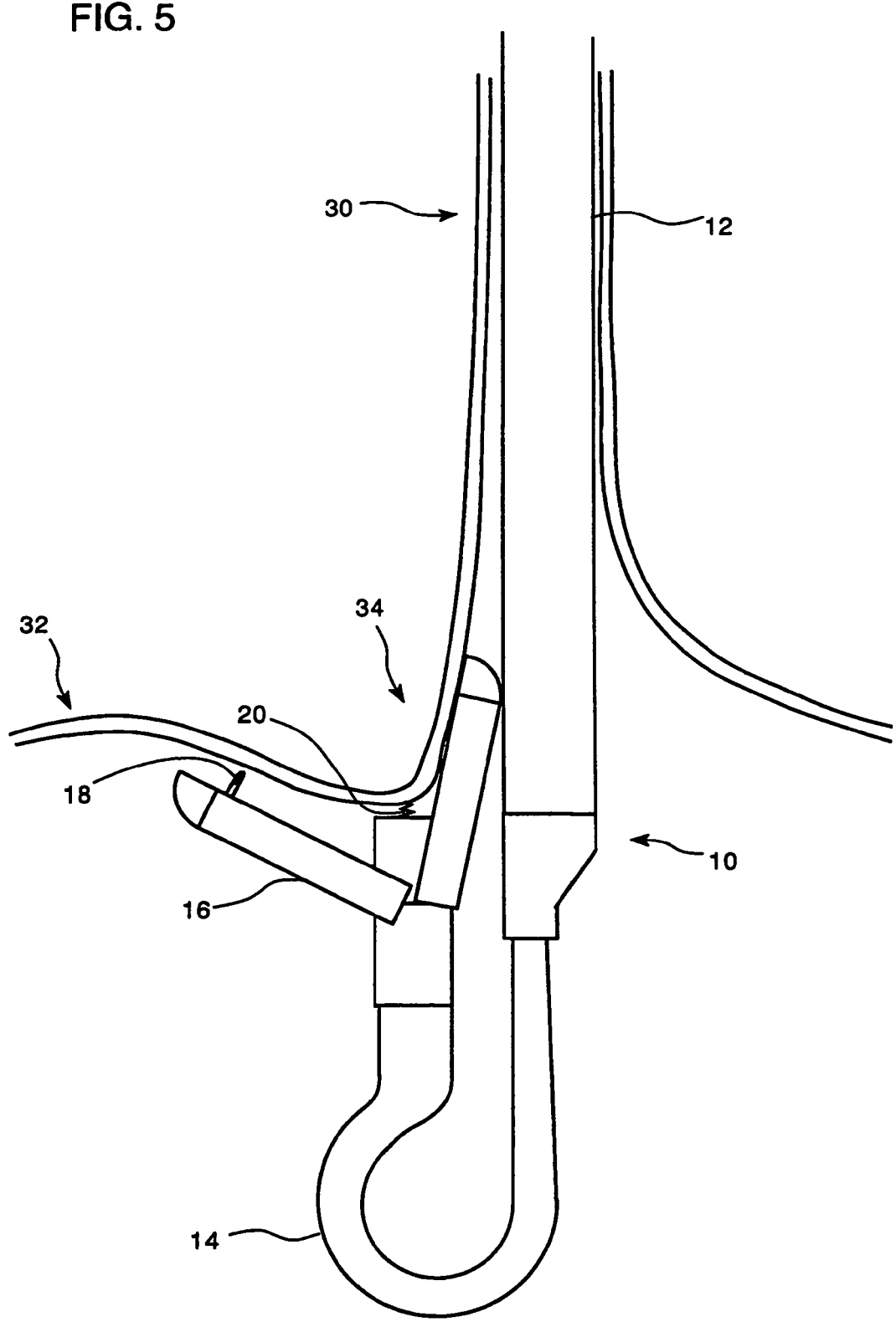
FIG. 5 is a side cross sectional view of a portion of the esophagus and a portion of the stomach, and a side view of the instrument in place in the esophagus and stomach, showing the retractor retracting the tissue.

FIG. 5 shows the instrument 10 in place in the esophagus 30 and the stomach 32, with the instrument 10 in a retroflexed position, the movable arms 16 in an open position, and the retractor 20 retracting the tissue at or near the junction 34 of the esophagus 30 and the stomach 32 into the space between the movable arms 16.

Figure 6:
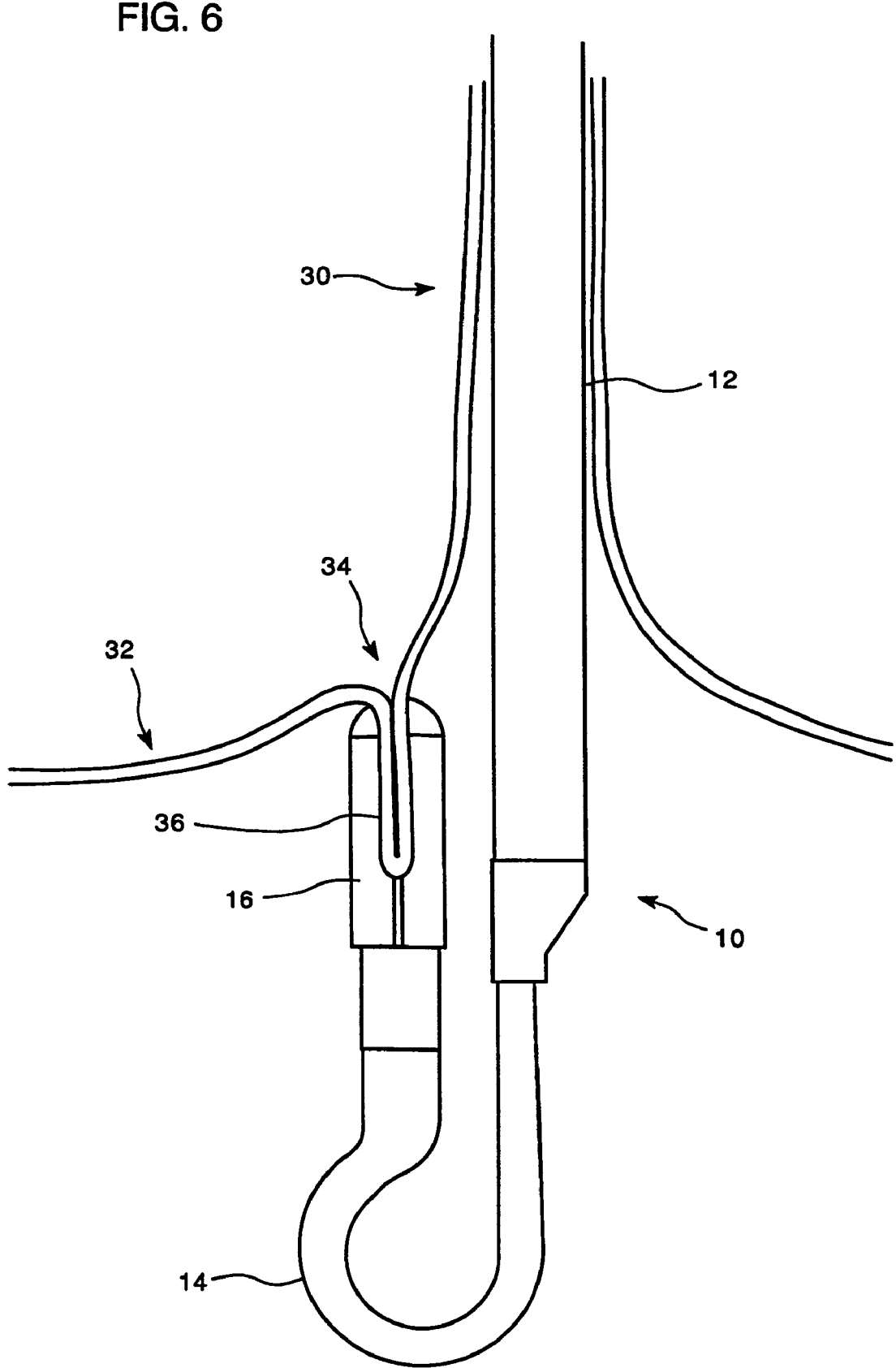
FIG. 6 is a side cross sectional view of a portion of the esophagus and a portion of the stomach, and a side view of the instrument in place in the esophagus and stomach, showing the movable arms closed, forming a tissue fold.

FIG. 6 shows the instrument 10 in place in the esophagus 30 and the stomach 32, with the instrument 10 in a retroflexed position, and the movable arms 16 closed, to create a fold 36 of tissue at or near the junction 34 of the esophagus 30 and the stomach 32. The mechanism to close movable arms is as is disclosed in the referenced patent applications.

FIG. 7 shows the instrument 10 in place in the esophagus 36 and the stomach 32, with the instrument 10 in a retroflexed position, and the movable arms 16 opened. An implant 22 has been placed through the tissue to maintain fixation of the tissue fold 36. Placement of the implant is accomplished as is disclosed in the referenced patent applications.

Figure 8:
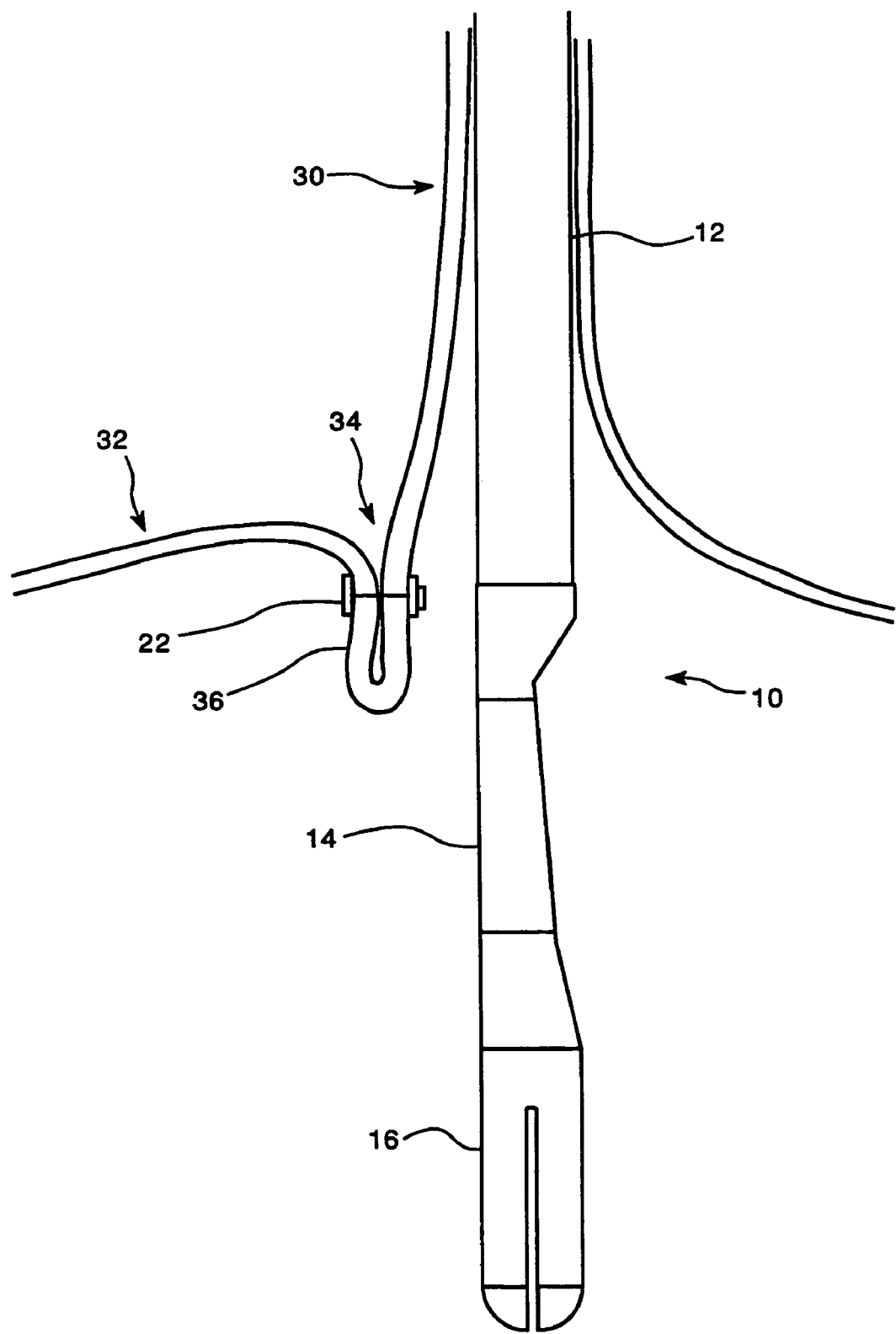
FIG. 8 is a side cross sectional view of a portion of the esophagus and a portion of the stomach, and a side view of the instrument in place in the esophagus and stomach, showing the tissue fold, with the instrument in a straight configuration for removal from the patient.

FIG. 8 shows the instrument 10 in place in the esophagus 30 and the stomach 32, with the instrument 10 in a straight position, and the movable arms 16 closed. The tissue fold 36 is shown, fixated by implant 22. The instrument 10 is in position for removal from the patient.

This invention provides a device and method which can be used to treat GERD by creating and fixating a fold of tissue at or near the junction of the esophagus and the stomach, thereby fixating the wall of the stomach to the wall of the esophagus. This invention allows this fold to be created and fixated via a completely endoluminal technique.

In another aspect of the invention, more than one fold is created in the tissue at or near the junction of the esophagus and the stomach.

In another aspect of the invention, the movable arms are attached to the retroflexing portion in a manner that allows the operator to rotate the position of the movable arms relative to the retroflexing portion about the center axis of the movable arms, thus allowing the operator to vary the orientation of the tissue fold.

While the invention has been described in detail with reference to the preferred embodiments thereof, it will be apparent to one skilled in the art that various changes and modifications can be made and equivalents employed, without departing from the present invention. For example, in the embodiment described above in conjunction with FIGS. 1-8, the moveable arms open and close in the same plane within which the retroflexing portion moves. However, it is appreciated that the plane in which the moveable arms open and close relative to the retroflexing portion can be at other orientations including angles between the same plane (i.e., 0.degree.) and a plane transverse (i.e., 90.degree.) to the plane within which the retroflexing portion moves. Indeed, in certain embodiments, the medical instrument can include a mechanism for allowing the user to adjust the angle of the moveable arms relative to the retroflexing portion.

What is claimed is:

1. A method comprising:
advancing an apparatus including an elongated member transorally into the stomach, the apparatus including a distal end effector having first and second members configured to engage tissue, the first and second members being movable relatively toward one another generally in a first plane, and
moving the distal end effector relative to the elongated member in a second plane that is substantially orthogonal to the first plane to position the first and second members for grasping tissue distal to a distal-most end of the distal end effector along a greater curvature of a stomach, at least one of the first and second members carrying a fixation device for fixing engaged portions of tissue together.

2. The method of claim 1, further comprising engaging tissue by moving the first and second members relatively toward one another generally in the first plane.

3. The method of claim 2, wherein the moving of the first and second members engages a first tissue section of the greater curvature of the stomach with a first securing part of the fixation-device and a second tissue section of the greater curvature of the stomach with a second securing part of the fixation device.

4. The method of claim 1, further comprising piercing the tissue with a third member of the distal end effector prior to engaging the tissue with the first and second members.

5. The method of claim 4, further comprising manipulating the tissue pierced by the third member into position between the first and second members.

6. The method of claim 1, wherein advancing an apparatus transorally into the stomach includes advancing a substantially flexible elongated member transorally into the stomach.

7. The method of claim 1, wherein advancing an apparatus transorally into the stomach includes advancing an elongated member disposed within an overtube transorally into the stomach.

8. A method for approximating tissue, comprising:
advancing an apparatus including an elongated flexible member into a body through a natural orifice, the apparatus including a distal end effector movable relative to the elongated flexible member and having first and second members configured to engage tissue, at least one of the first and second members being movable relative to the other generally in a first plane;
orienting the flexible elongated member into a desired location near a desired surgical site;
visualizing at least the first and second members as they are moved into position to engage tissue;
grasping substantially concave tissue to be approximated distal to a distal-most end of the distal end effector using the first and second members;
manipulating the grasped tissue into a desired configuration; and
approximating the grasped tissue using a fixation device deployed from at least one of the first and second members.

9. The method of claim 8, further including advancing a tissue retractor to engage tissue and retract the engaged tissue into position between the first and second members.

10. The method of claim 9, wherein advancing the tissue retractor includes advancing one of a corkscrew-like retractor, a grasper retractor, and a suction retractor to retract tissue into position between the first and second members.

11. The method of claim 8, wherein approximating the grasped tissue includes applying a biocompatible fastener selected from the group consisting of a staple, a clip, a tack, a rivet, a two-part fastener, a helical fastener, a suture, and a T-bar suture.

12. The method of claim 8, wherein visualizing includes endoscopically visualizing at least a portion of at least one of the steps of advancing, grasping, manipulating, and approximating.

13. The method of claim 8, wherein advancing the elongate flexible shaft includes advancing the elongate flexible shaft disposed within an overtube.

14. The method of claim 8, wherein manipulating the grasped tissue into a desired configuration includes manipulating the grasped tissue to form a tissue bulge.

15. A method comprising:
advancing an apparatus including an elongated member transorally into the stomach, the apparatus including a distal end effector movable relative to the elongated member and having first and second members configured to engage tissue, the first and second members being movable relatively toward one another generally in a first plane, at least one of the first and second members carrying a fixation device for fixing engaged portions of tissue together;
grasping tissue distal to a distal-most end of the distal end effector along a greater curvature of the stomach; and
plicating the tissue of the stomach with the fixation device to reduce a volume of the stomach.

16. The method of claim 15, further comprising moving the first and second members relatively toward one another to grasp two portions of tissue along the greater curvature of the stomach to form a fold of tissue along the greater curvature.

17. The method of claim 15, further including advancing a tissue retractor to engage tissue and retract the engaged tissue into position between the first and second members.

18. The method of claim 17, wherein advancing the tissue retractor includes advancing one of a corkscrew-like retractor, a grasper retractor, and a suction retractor to retract tissue into position between the first and second members.

19. The method of claim 15, wherein plicating the tissue of the stomach with the fixation device comprises applying a biocompatible fixation device selected from the group consisting of a staple, a clip, a tack, a rivet, a two-part fastener, a helical fastener, a suture, and a T-bar suture.

20. The method of claim 15, further comprising endoscopically visualizing at least a portion of at least one of the steps of advancing, grasping, and plicating.

\* \* \* \* \*